US007211386B2

(12) United States Patent
Small et al.

(10) Patent No.: US 7,211,386 B2
(45) Date of Patent: May 1, 2007

(54) ALPHA-2A-ADRENERGIC RECEPTOR POLYMORPHISMS

(75) Inventors: Kersten M. Small, Cincinnati, OH (US); Stephen B. Liggett, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 399 days.

(21) Appl. No.: 10/638,714

(22) Filed: Aug. 11, 2003

(65) Prior Publication Data

US 2005/0074772 A1   Apr. 7, 2005

Related U.S. Application Data

(62) Division of application No. 09/636,259, filed on Aug. 10, 2000, now abandoned.

(51) Int. Cl.
*C12Q 1/68* (2006.01)
*C07H 21/02* (2006.01)
*C07H 21/04* (2006.01)

(52) U.S. Cl. .................... 435/6; 435/91.2; 536/23.5
(58) Field of Classification Search ............... None
See application file for complete search history.

(56) References Cited

U.S. PATENT DOCUMENTS

| | | | |
|---|---|---|---|
| 5,595,880 | A | 1/1997 | Weinshank et al. |
| 5,648,482 | A | 7/1997 | Meyer |
| 5,846,710 | A | 12/1998 | Bajaj |
| 5,856,092 | A | 1/1999 | Dale et al. |
| 5,888,819 | A | 3/1999 | Goelet et al. |
| 5,981,174 | A | 11/1999 | Wolf et al. |
| 6,004,744 | A | 12/1999 | Goelet et al. |
| 6,013,431 | A | 1/2000 | Soderlund et al. |
| 6,156,503 | A | 12/2000 | Drazen et al. |

FOREIGN PATENT DOCUMENTS

WO    WO 0129082    4/2001

OTHER PUBLICATIONS

Idoia Martin-Guerrero et al. The N251K function polymoprhism in the alpha-2A adrenoceptor gene is not associated with depression: a study in suicide completers. Dec. 2005, Pyschopharmacology vol. 184: 82-86.*
Kersten Small et al. Identification and functional characterization of alpha-2 adrenoceptor polymorphisms. Sep. 2001, TRENDS in Pharmacological Sciences vol. 222, No. 9, 471-477.*
Heinonen P. et al: "Identification of a three-amino acid deletion in the alpha2B-adrenergic receptor that is associated with reduced basal metabolic rate in obese subjects." *The Journal of Clinical Endocrinology and Metabolism*, United States, Jul. 1999, vol. 84, No. 7, pp. 2429-2433.
Baldwin C.T., et al: "Identification of a polymorphic glutamic acid stretch in the alpha2B-adrenergic receptor and lack of linkage with essential hypertension." *American Journal of Hypertension: Journal of the American Society of Hypertension*, United States, Sep. 1999, vol.12, No. 9, Pt. 1, pp. 853-857.
Jewell-Motz, E.A. et al: "An acidic motif within the third intracellular loop of the alpha2C2 adrenergic receptor is required for agonist-promoted phosphorylation and desensitization." *Biochemistry*, United States Sep. 19, 1995, vol. 34, No. 37, Sep. 19, 1995, pp. 11946-11953.
Comings, D.E., et al: "Additive effect of three noradrenergic genes (ADRA2a, ADRA2C, DBH) on attention-deficit hyperactivity disorder and learning disabilities in Tourette syndrome subjects." *Clinical Genetics*, Denmark, Mar. 1999, vol. 55, No. 3, pp. 160-172.
Makaritsis K.P., et al: "Role of the alpha2B-adrenergic receptor in the development of salt-induced hypertension." *Hypertension*. United States, Jan. 1999, vol. 33, No. 1, Jan. 1999, pp. 14-17.
Michel M.C., et al: "Functional correlates of alpha(2A)-adrenoceptor gene polymorphism in the HANE study." *Nephrology, Dialysis, Transplantation: Official Publication of the European Dialysis and Transplant Association-European Renal Association*. England, Nov. 1999, vol. 14, No. 11, pp. 2657-2663.
Freeman K., et al: "Genetic polymorphism of the alpha 2-adrenergic receptor is associated with increased platelet aggregation, baroreceptor sensitivity, and salt excretion in normotensive humans." *American Journal of Hypertension: Journal of the American Society of Hypertension*. United States, Sep. 1995, vol. 8, No. 9, pp. 863-869.
Small K.M., et al: "Polymorphic deletion of three intracellular acidic residues of the alpha 2B-adrenergic receptor decreases G protein-coupled receptor kinase-mediated phosphorylation and desensitization." *The Journal of Biological Chemistry*, United States, Feb. 16, 2001, vol. 276, No. 7, pp. 4917-4922.
Snapir A., et al: "An insertion/deletion polymorphism in the alpha2B-adrenergic receptor gene is a novel genetic risk factor for acute coronary events." *Journal of the American College of Cardiology*. United States, May 2001, vol. 37, No. 6, pp. 1516-1522.
Limbird, L.E. (1988) FASEB J 2, 2686-2695.
Luttrell, L.M., van Biesen, T., Hawes, B.E., Della Rocca, G.J., Luttrell, D.K., and Lefkowitz, R.J. (1998) in Catecholamines: Bridging Basic Science with Clinical Medicine (Goldstein, D.S., Eisenhofer, G., and McCarty, R., eds) pp. 466-470, Academic Press.
Ruffolo, R.R., Jr., Nicholas, A.J., Stadel, J.M., and Hieble, J.P. (1993) Annu Rev Pharmacol Toxicol 32, 243-279.
Hein, L., Altman, J.D., and Kobilka, B.K. (1999) Nature 402, 1810-184.

(Continued)

*Primary Examiner*—Ram R. Shukla
*Assistant Examiner*—Amanda Shaw
(74) *Attorney, Agent, or Firm*—Fenwick + West

(57) ABSTRACT

The present invention includes polymorphisms in nucleic acids encoding the alpha-2A adrenergic receptor and expressed alpha-2A adrenergic receptor molecule. The invention also pertains to methods and molecules for detecting such polymorphisms and transgenic animals expressing alpha-2A adrenergic receptor molecules. The invention further pertains to the use of such molecules and methods in the diagnosis, prognosis, and treatment of diseases such as cardiovascular and central nervous system diseases.

5 Claims, 6 Drawing Sheets

OTHER PUBLICATIONS

Altman J.D., Trendelenburg, A.U., MacMillan, L., Bernstein, D., Limbird, L., Starke, K., Kobilka, B.K., and Hein, L. (1999) Mol. Pharmacol. 56, 154-161.

Lakhlani, P.P., MacMillan, L.B., Guo, T.Z., McCool, B.a., Lovinger, D.M., Maze, M., and Limbird, L.E. (1997) Proc Natl Acad Sci USA 94, 9950-9955.

Holmes, B., Brogden, R.N., Heel, R.C., Speight, T.M., and Avery, G.S. (1983) Drugs 26, 212-229.

Dao, T.T., Kailasam, M.T., Parmer, R.J., Le, H.V., Le Verge, R., Kennedy, B.P., Ziegler, G., Insel, P.A., Wright, F.A., and O'Connor, D.T. (1998) J Hypertens 16, 779-792.

Goldstein, D.S., Grossman, E., Listwak, S., and Folio, C.J. (1991) Hypertension 18, III40-III48.

Lockette, W., Ghosh, S., Farrow, S., MacKenzie, S., Baker, S., Miles, P., Schork, A., and Cadaret, L. (1995) Am J Hypertens 8, 390-394.

Svetkey, L.P., Timmons, P.Z., Emovon, O., Anderson, N.B., Preis, L., and Chen, T.-T. (1996) Hypertension 27, 1210-1215.

Liggett, S.B. (1998) Clin and Exp.Allergy 28, 77-79.

Guyer, C.A., Horstman, D.A., Wilson, A.L., Clark, J.D., Cragoe, E.J.Jr., and Limbird, L.E. (1990) J Biol Chem 265, 17307-17317.

Rutkowski, M.P., Klanke, C.A., Su, Y.R., Reif, M., and Menon, A.G. (1998) Hypertension 31, 1230-1234.

Eason, M.G. and Liggett, S.B. (1992) J.Biol.Chem. 267, 25473-25479.

Jewell-Motz, E.A. and Liggett, S.B. (1996) J.Biol.Chem 271, 18082-18087.

de chasseval, R. and de Villartay, J.-P. (1991) Nucleic Acids Research 20, 245-250.

Eason, M.G., Moreira, S.P., and Liggett, S.B. (1995) J.Biol. Chem. 270, 4681-4688.

Jewell-Motz, E.A., Donnelly, E.T., Eason, M.G., and Liggett, S.B. (1998) Biochem 37, 15720-15725.

Schwinn, D.A., Page, S.O., Middleton, J.P., Lorenz, W., Liggett, S.B., Yamamoto, K., Carou, M.G., Lefkowitz, R.J., and Cotecchia, S. (1991) Mol. Pharmacol. 40, 619-626.

Martin, T.F.J. (1983) J Biol Chkem 258, 14816-14822.

Eason, M.G., Jacinto, M.T., Theiss, C.T., and Liggett, S.B. (1994) Proc.Natl.Acad.Sci., USA 91, 11178-11182.

Smith, P.K., Krohn, R.I., Hermanson, G.T., Mallia, A.K., Gartner, F.H., Provenzano, M.D., Fujimoto, E.K., Goeke, N.M., Olson, B.J., and Klenk, D.C. (1985) Anal.Biochem. 150, 76-85.

Eason, M.G. and Liggett, S.B. (1996) J.Biol.Chem. 271, 12826-12832.

Exton, J.H. (1996) Annu Rev Pharmacol Toxicol 36, 481-509.

MacMillan, L.B., Lakhlani, P., Lovinger, D., and Limbird, L.E. (1998) Recent Prog Horm Res 53, 25-42.

Makaritsis, K.P., Johns, C., Gavras, I., Altman, J.D., Handy, D.E., Brenshan, M.R., and Gavras, H. (1999) Hypertension 34, 403-407.

Spiegel, A.M. (1996) Annu Rev Physiol 58, 143-170.

Kotanko, P., Binder, A., Tasker, J., DeFreitas, P., Kamdar, S./, Clark, A.J., Skrabal, F., and Caulfield, M. (1997) Hypertension 30, 773-776.

Liggett, S.B., Wagoner, L.E., Craft, L.L., Hornung, R.W., Hoit, B.D., McIntosh, T.C., and Walsh, R.A. (1998) J. Clin Invest 102, 1534-1539.

Tan, S., Hall, L.P., Dewar, J., Dow, E., and Lipworth, B. (1997) Lancet 350, 995-999.

Green, S.A., Cole, G., Jacinto, M., Innis, M., and Liggett, S.B. (1993) J Biol Chem 268, 23116-23121.

Shenker, A., Laue, L., Kosugi, S., Mcrendino, J.J., Minegishi, T., and Cutler, G.B. (1993) Nature Lond 365, 652-654.

Fraser, C.M. et al. Cloning, sequence analysis, and permanent expression of a human alpha2-adrenergic receptor in Chinese hamster ovary cells. The Journal of Biological Chemistry 264(20): 11754-11761 (Jul. 1989).

Feng, J. et al. Variants in the alpha2A AR adrenergic receptor gene in psychiatric patients. American Journal of Medical Genetics (Neuropsychiatric Genetics) 81:405-410 (1998).

Guyer, C.A. et al. Cloning, sequencing, and expression of the gene encoding the procine alpha2-adrenergic receptor. The Journal of Biological Chemistry 265(28):17307-17317 (Oct. 1990).

Small, K.M. et al. An Asn to Lys polymophism in the third intracellular loop of the human alpha2A-adrenergic receptor imparts enhanced agonist-promoted Gi coupling. The Journal of Biological Chemistry 275(49):38518-38523 (Dec. 2000).

Kobilka, B.K. et al. Cloning, sequencing, and expression of the gene coding for the human platelet alpha2-adrenergic receptor. Science 238:650-656 (Oct. 1987).

* cited by examiner

| | 257 | | | | | | 251 | | | | | | 245 | |
|---|---|---|---|---|---|---|---|---|---|---|---|---|---|---|
| HUMAN | R | E | P | G | L | G | N/K | P | R | R | E | T | G | (SEQ. ID NO: 20) |
| | | | | | | | | | | | | | | (SEQ. ID NO: 21) |
| MOUSE | R | E | P | G | L | G | N | P | R | R | D | A | G | (SEQ ID NO: 22) |
| RAT | R | E | P | G | V | A | N | P | R | R | D | A | G | (SEQ ID NO: 23) |
| GUINES PIG | R | E | L | G | L | G | N | P | R | R | E | A | G | (SEQ ID NO: 24) |
| BOS TAURUS | R | E | P | G | L | G | N | P | R | R | E | A | S | (SEQ ID NO: 25) |
| PIG | R | E | P | G | L | G | N | P | R | R | E | A | G | (SEQ ID NO: 26) |

FIG. 2

SEQUENCE LISTING

<160> NUMBER OF SEQ ID NOS: 26

<210> SEQ ID NO 1
<211> LENGTH: 1350
<212> TYPE: DNA
<213> ORGANISM: Homo sapiens

<400> SEQUENCE: 1

```
atgggctccc tgcagccgga cgcgggcaac gcgagctgga acgggaccga ggcgccgggg       60
ggcggcgccc gggccacccc ttactccctg caggtgacgc tgacgctggt gtgcctggcc      120
ggcctgctca tgctgctcac cgtgttcggc aacgtgctcg tcatcatcgc cgtgttcacg      180
agccgcgcgc tcaaggcgcc ccaaaacctc ttcctggtgt ctctggcctc ggccgacatc      240
ctggtggcca cgctcgtcat ccctttctcg ctggccaacg aggtcatggg ctactggtac      300
ttcggcaagg cttggtgcga gatctacctg gcgctcgacg tgctcttctg cacgtcgtcc      360
atcgtgcacc tgtgcgccat cagcctggac cgctactggt ccatcacaca ggccatcgag      420
tacaacctga agcgcacgcc gcgccgcatc aaggccatca tcatccgtgt gtgggtcatc      480
tcggccgtca tctccttccc gccgctcatc tccatcgaga agaagggcgg cggcggcggc      540
ccgcagccgg ccgagccgcg ctgcgagatc aacgaccaga gtggtacgt catctcgtcg      600 tgcatcggct ccttcttcgc tccctgcctc atcatgatcc tggtctacgt gcgcatctac      660
cagatcgcca agcgtcgcac ccgcgtgcca cccagccgcc ggggtccgga cgccgtcgcc      720
gcgccgccgg ggggcaccga gcgcaggccc aacggtctgg gccccgagcg cagcgcgggc      780 ccgggggggcg cagaggccga accgctgccc acccagctca acggcgcccc tggcgagccc      840
gcgccggccg ggccgcgcga caccgacgcg ctggacctgg aggagagctc gtcttccgac      900
cacgccgagc ggcctccagg gccccgcaga cccgagcgcg gtccccgggg caaaggcaag      960
gcccgagcga gccaggtgaa gccgggcgac agcctgccgc ggcgcgggcc ggggcgacg     1020 gggatcggga cgccggctgc agggccgggg gaggagcgcg tcggggctgc caaggcgtcg     1080
```

```
cgctggcgcg ggcggcagaa ccgcgagaag cgcttcacgt tcgtgctggc cgtggtcatc    1140
ggagtgttcg tggtgtgctg gttccccttc ttcttcacct acacgctcac ggccgtcggg    1200
tgctccgtgc cacgcacgct cttcaaattc ttcttctggt tcggctactg caacagctcg    1260
ttgaacccgg tcatctacac catcttcaac cacgatttcc gccgcgcctt caagaagatc    1320
ctctgtcggg gggacaggaa gcggatcgtg                                     1350

<210> SEQ ID NO 2
<211> LENGTH: 1350
<212> TYPE: DNA
<213> ORGANISM: Homo sapiens

<400> SEQUENCE: 2
atgggctccc tgcagccgga cgcgggcaac gcgagctgga cgggaccga ggcgccgggg     60 ggcggcgccc gggccacccc ttactccctg caggtgacgc tgacgctggt gtgcctggcc    120
ggcctgctca tgctgctcac cgtgttcggc aacgtgctcg tcatcatcgc cgtgttcacg    180
agccgcgcgc tcaaggcgcc ccaaaacctt ccctggtgt ctctggcctc ggccgacatc     240
ctggtggcca cgctcgtcat ccctttctcg ctggccaacg aggtcatggg ctactggtac    300
tcggcaaggg cttggtgcga gatctacctg cgctcgacg tgctcttctg cacgtcgtcc    360
atcgtgcacc tgtgcgccat cagcctggac cgctactggc ccatcacaca ggccatcgag    420
tacaacctga gcgcacgcc gcgccgcatc aaggccatca tcatcaccgt gtgggtcatc    480
tcggccgtca tctccttccc gccgctcatc tccatcgaga agaagggcgg cggcggcggc    540
ccgcagccgg ccgagccgcg ctgcgagatc aacgaccaga gtggtacgt catctcgtcg    600 tgcatcggct ccttcttcgc tccctgcctc atcatgatcc tggtctacgt gcgcatctac    660
cagatcgcca agcgtcgcac ccgcgtgcca cccagccgcc ggggtccgga cgccgtcgcc    720
gcgccgccgg gggcaccgga gcgcaggcc aagggtctgg cccccgagcg cagcgcgggc    780 ccgggggggcg cagaggccga accgctgccc acccagctca acggcgcccc tggcgagccc    840
gcgccggccc ggccgcgcga caccgacgcg ctggacctgg aggagagctc gtcttccgac    900
cacgccgagc ggcctccagg gccccgcaga cccgagcgcg gtccccgggg caaaggcaag    960 gccccgagcga gccaggtgaa gccgggcgac agcctgccgc ggcgcgggcc ggggcgacg    1020 gggatcggga cgccggctgc agggccgggg gaggagcgcg tcgggctgc caaggcgtcg    1080 cgctggcgcg ggcggcagaa ccgcgagaag cgcttcacgt tcgtgctggc cgtggtcatc    1140
ggagtgttcg tggtgtgctg gttccccttc ttcttcacct acacgctcac ggccgtcggg    1200
tgctccgtgc cacgcacgct cttcaaattc ttcttctggt tcggctactg caacagctcg    1260
ttgaacccgg tcatctacac catcttcaac cacgatttcc gccgcgcctt caagaagatc    1320
ctctgtcggg gggacaggaa gcggatcgtg                                     1350

<210> SEQ ID NO 3
<211> LENGTH: 450
<212> TYPE: PRT
<213> ORGANISM: Homo sapiens

<400> SEQUENCE: 3

Met Gly Ser Leu Gln Pro Asp Ala Gly Asn Ala Ser Trp Asn Gly Thr
1               5                   10                  15

Glu Ala Pro Gly Gly Gly Ala Arg Ala Thr Pro Tyr Ser Leu Gln Val
            20                  25                  30
```

```
Thr Leu Thr Leu Val Cys Leu Ala Gly Leu Met Leu Leu Thr Val
        35                  40                  45

Phe Gly Asn Val Leu Val Ile Ile Ala Val Phe Thr Ser Arg Ala Leu
        50                  55                  60

Lys Ala Pro Gln Asn Leu Phe Leu Val Ser Leu Ala Ser Ala Asp Ile
 65              70                  75                  80

Leu Val Ala Thr Leu Val Ile Pro Phe Ser Leu Ala Asn Glu Val Met
                85                  90                  95

Gly Tyr Trp Tyr Phe Gly Lys Ala Trp Cys Glu Ile Tyr Leu Ala Leu
            100                 105                 110

Asp Val Leu Phe Cys Thr Ser Ser Ile Val His Leu Cys Ala Ile Ser
        115                 120                 125

Leu Asp Arg Tyr Trp Ser Ile Thr Gln Ala Ile Glu Tyr Asn Leu Lys
        130                 135                 140

Arg Thr Pro Arg Arg Ile Lys Ala Ile Ile Thr Val Trp Val Ile
145                 150                 155                 160

Ser Ala Val Ile Ser Phe Pro Pro Leu Ile Ser Ile Glu Lys Lys Gly
                165                 170                 175

Gly Gly Gly Gly Pro Gln Pro Ala Glu Pro Arg Cys Glu Ile Asn Asp
            180                 185                 190

Gln Lys Trp Tyr Val Ile Ser Ser Cys Ile Gly Ser Phe Phe Ala Pro
        195                 200                 205

Cys Leu Ile Met Ile Leu Val Tyr Val Arg Ile Tyr Gln Ile Ala Lys
        210                 215                 220

Arg Arg Thr Arg Val Pro Pro Ser Arg Arg Gly Pro Asp Ala Val Ala
225                 230                 235                 240

Ala Pro Pro Gly Gly Thr Glu Arg Arg Pro Asn Gly Leu Gly Pro Glu
            245                 250                 255

Arg Ser Ala Gly Pro Gly Gly Ala Glu Ala Glu Pro Leu Pro Thr Gln
        260                 265                 270

Leu Asn Gly Ala Pro Gly Glu Pro Ala Pro Ala Gly Pro Arg Asp Thr
        275                 280                 285

Asp Ala Leu Asp Leu Glu Glu Ser Ser Ser Ser Asp His Ala Glu Arg
        290                 295                 300

Pro Pro Gly Pro Arg Arg Pro Glu Arg Gly Pro Arg Gly Lys Gly Lys
305                 310                 315                 320

Ala Arg Ala Ser Gln Val Lys Pro Gly Asp Ser Leu Pro Arg Arg Gly
            325                 330                 335

Pro Gly Ala Thr Gly Ile Gly Thr Pro Ala Ala Gly Pro Gly Glu Glu
            340                 345                 350

Arg Val Gly Ala Ala Lys Ala Ser Arg Trp Arg Gly Arg Gln Asn Arg
            355                 360                 365

Glu Lys Arg Phe Thr Phe Val Leu Ala Val Val Ile Gly Val Phe Val
        370                 375                 380

Val Cys Trp Phe Pro Phe Phe Thr Tyr Thr Leu Thr Ala Val Gly
385                 390                 395                 400

Cys Ser Val Pro Arg Thr Leu Phe Lys Phe Phe Phe Trp Phe Gly Tyr
                405                 410                 415

Cys Asn Ser Ser Leu Asn Pro Val Ile Tyr Thr Ile Phe Asn His Asp
            420                 425                 430

Phe Arg Arg Ala Phe Lys Lys Ile Leu Cys Arg Gly Asp Arg Lys Arg
        435                 440                 445

Ile Val
```

-continued

450

<210> SEQ ID NO 4
<211> LENGTH: 450
<212> TYPE: PRT
<213> ORGANISM: Homo sapiens

<400> SEQUENCE: 4

| | | | | | | | | | | | | | | |
|---|---|---|---|---|---|---|---|---|---|---|---|---|---|---|
| Met | Gly | Ser | Leu | Gln | Pro | Asp | Ala | Gly | Asn | Ala | Ser | Trp | Asn | Gly | Thr |
| 1 | | | | 5 | | | | | 10 | | | | | 15 | |
| Glu | Ala | Pro | Gly | Gly | Ala | Arg | Ala | Thr | Pro | Tyr | Ser | Leu | Gln | Val | |
| | | | 20 | | | | | 25 | | | | | 30 | | |
| Thr | Leu | Thr | Leu | Val | Cys | Leu | Ala | Gly | Leu | Leu | Met | Leu | Leu | Thr | Val |
| | | | 35 | | | | | 40 | | | | | 45 | | |
| Phe | Gly | Asn | Val | Leu | Val | Ile | Ile | Ala | Val | Phe | Thr | Ser | Arg | Ala | Leu |
| | 50 | | | | | 55 | | | | | 60 | | | | |
| Lys | Ala | Pro | Gln | Asn | Leu | Phe | Leu | Val | Ser | Leu | Ala | Ser | Ala | Asp | Ile |
| 65 | | | | | 70 | | | | | 75 | | | | | 80 |
| Leu | Val | Ala | Thr | Leu | Val | Ile | Pro | Phe | Ser | Leu | Ala | Asn | Glu | Val | Met |
| | | | | 85 | | | | | 90 | | | | | 95 | |
| Gly | Tyr | Trp | Tyr | Phe | Gly | Lys | Ala | Trp | Cys | Glu | Ile | Tyr | Leu | Ala | Leu |
| | | | | 100 | | | | | 105 | | | | | 110 | |
| Asp | Val | Leu | Phe | Cys | Thr | Ser | Ser | Ile | Val | His | Leu | Cys | Ala | Ile | Ser |
| | | | 115 | | | | | 120 | | | | | 125 | | |
| Leu | Asp | Arg | Tyr | Trp | Ser | Ile | Thr | Gln | Ala | Ile | Glu | Tyr | Asn | Leu | Lys |
| | 130 | | | | | 135 | | | | | 140 | | | | |
| Arg | Thr | Pro | Arg | Arg | Ile | Lys | Ala | Ile | Ile | Thr | Val | Trp | Val | Ile | |
| 145 | | | | | 150 | | | | | 155 | | | | | 160 |
| Ser | Ala | Val | Ile | Ser | Phe | Pro | Pro | Leu | Ile | Ser | Ile | Glu | Lys | Lys | Gly |
| | | | | 165 | | | | | 170 | | | | | 175 | |
| Gly | Gly | Gly | Gly | Pro | Gln | Pro | Ala | Glu | Pro | Arg | Cys | Glu | Ile | Asn | Asp |
| | | | 180 | | | | | 185 | | | | | 190 | | |
| Gln | Lys | Trp | Tyr | Val | Ile | Ser | Ser | Cys | Ile | Gly | Ser | Phe | Phe | Ala | Pro |
| | | 195 | | | | | 200 | | | | | 205 | | | |
| Cys | Leu | Ile | Met | Ile | Leu | Val | Tyr | Val | Arg | Ile | Tyr | Gln | Ile | Ala | Lys |
| 210 | | | | | 215 | | | | | 220 | | | | | |
| Arg | Arg | Thr | Arg | Val | Pro | Pro | Ser | Arg | Arg | Gly | Pro | Asp | Ala | Val | Ala |
| 225 | | | | | 230 | | | | | 235 | | | | | 240 |
| Ala | Pro | Pro | Gly | Gly | Thr | Glu | Arg | Arg | Pro | Lys | Gly | Leu | Gly | Pro | Glu |
| | | | | 245 | | | | | 250 | | | | | 255 | |
| Arg | Ser | Ala | Gly | Pro | Gly | Gly | Ala | Glu | Ala | Glu | Pro | Leu | Pro | Thr | Gln |
| | | | 260 | | | | | 265 | | | | | 270 | | |
| Leu | Asn | Gly | Ala | Pro | Gly | Glu | Pro | Ala | Pro | Ala | Gly | Pro | Arg | Asp | Thr |
| | | 275 | | | | | 280 | | | | | 285 | | | |
| Asp | Ala | Leu | Asp | Leu | Glu | Glu | Ser | Ser | Ser | Asp | His | Ala | Glu | Arg | |
| | 290 | | | | | 295 | | | | | 300 | | | | |
| Pro | Pro | Gly | Pro | Arg | Arg | Pro | Glu | Arg | Gly | Pro | Arg | Gly | Lys | Gly | Lys |
| 305 | | | | | 310 | | | | | 315 | | | | | 320 |
| Ala | Arg | Ala | Ser | Gln | Val | Lys | Pro | Gly | Asp | Ser | Leu | Pro | Arg | Arg | Gly |
| | | | | 325 | | | | | 330 | | | | | 335 | |
| Pro | Gly | Ala | Thr | Gly | Ile | Gly | Thr | Pro | Ala | Ala | Gly | Pro | Gly | Glu | Glu |
| | | | 340 | | | | | 345 | | | | | 350 | | |
| Arg | Val | Gly | Ala | Ala | Lys | Ala | Ser | Arg | Trp | Arg | Gly | Arg | Gln | Asn | Arg |
| | | | | 355 | | | | | 360 | | | | | 365 | |

-continued

```
Glu Lys Arg Phe Thr Phe Val Leu Ala Val Val Ile Gly Val Phe Val
    370                 375                 380

Val Cys Trp Phe Pro Phe Phe Thr Tyr Thr Leu Thr Ala Val Gly
385                 390                 395                 400

Cys Ser Val Pro Arg Thr Leu Phe Lys Phe Phe Trp Phe Gly Tyr
                405                 410                 415

Cys Asn Ser Ser Leu Asn Pro Val Ile Tyr Thr Ile Phe Asn His Asp
            420                 425                 430

Phe Arg Arg Ala Phe Lys Lys Ile Leu Cys Arg Gly Asp Arg Lys Arg
        435                 440                 445

Ile Val
    450

<210> SEQ ID NO 5
<211> LENGTH: 22
<212> TYPE: DNA
<213> ORGANISM: Homo sapiens

<400> SEQUENCE: 5
tttacccatc ggctctccct ac                                            22

<210> SEQ ID NO 6
<211> LENGTH: 23
<212> TYPE: DNA
<213> ORGANISM: Homo sapiens

<400> SEQUENCE: 6
gagacaccag gaagaggttt tgg                                           23

<210> SEQ ID NO 7
<211> LENGTH: 20
<212> TYPE: DNA
<213> ORGANISM: Homo sapiens

<400> SEQUENCE: 7
tcgtcatcat cgccgtgttc                                               20

<210> SEQ ID NO 8
<211> LENGTH: 23
<212> TYPE: DNA
<213> ORGANISM: Homo sapiens

<400> SEQUENCE: 8
cgtaccactt ctggtcgttg atc                                           23

<210> SEQ ID NO 9
<211> LENGTH: 24
<212> TYPE: DNA
<213> ORGANISM: Homo sapiens

<400> SEQUENCE: 9
gccatcatca tcaccgtgtg ggtc                                          24

<210> SEQ ID NO 10
<211> LENGTH: 23
<212> TYPE: DNA
<213> ORGANISM: Homo sapiens

<400> SEQUENCE: 10
ggctcgctcg ggccttgcct ttg                                           23
```

```
<210> SEQ ID NO 11
<211> LENGTH: 22
<212> TYPE: DNA
<213> ORGANISM: Homo sapiens

<400> SEQUENCE: 11
gacctggagg agagctcgtc tt                                              22

<210> SEQ ID NO 12
<211> LENGTH: 23
<212> TYPE: DNA
<213> ORGANISM: Homo sapiens

<400> SEQUENCE: 12
tgaccgggtt caacgagctg ttg                                             23

<210> SEQ ID NO 13
<211> LENGTH: 23
<212> TYPE: DNA
<213> ORGANISM: Homo sapiens

<400> SEQUENCE: 13
gccacgcacg ctcttcaaat tct                                             23

<210> SEQ ID NO 14
<211> LENGTH: 22
<212> TYPE: DNA
<213> ORGANISM: Homo sapiens

<400> SEQUENCE: 14
ttcccttgta ggagcagcag ac                                              22

<210> SEQ ID NO 15
<211> LENGTH: 18
<212> TYPE: DNA
<213> ORGANISM: Homo sapiens

<400> SEQUENCE: 15
tgtaaaacga cggccagt                                                   18

<210> SEQ ID NO 16
<211> LENGTH: 18
<212> TYPE: DNA
<213> ORGANISM: Homo sapiens

<400> SEQUENCE: 16
caggaaacag ctatgacc                                                   18

<210> SEQ ID NO 17
<211> LENGTH: 15
<212> TYPE: DNA
<213> ORGANISM: Homo sapiens

<400> SEQUENCE: 17
gcccaacggt ctggg                                                      15

<210> SEQ ID NO 18
<211> LENGTH: 15
<212> TYPE: DNA
<213> ORGANISM: Homo sapiens

<400> SEQUENCE: 18
gcccaagggt ctggg                                                      15
```

```
<210> SEQ ID NO 19
<211> LENGTH: 15
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n = a, c, g or t

<400> SEQUENCE: 19
gcccaanggt ctggg                                                      15

<210> SEQ ID NO 20
<211> LENGTH: 13
<212> TYPE: PRT
<213> ORGANISM: Homo sapiens

<400> SEQUENCE: 20

Arg Glu Pro Gly Leu Gly Asn Pro Arg Arg Glu Thr Gly
1               5                   10

<210> SEQ ID NO 21
<211> LENGTH: 13
<212> TYPE: PRT
<213> ORGANISM: Homo sapiens

<400> SEQUENCE: 21

Arg Glu Pro Gly Leu Gly Lys Pro Arg Arg Glu Thr Gly
1               5                   10

<210> SEQ ID NO 22
<211> LENGTH: 13
<212> TYPE: PRT
<213> ORGANISM: Mouse

<400> SEQUENCE: 22

Arg Glu Pro Gly Leu Gly Asn Pro Arg Arg Asp Ala Gly
1               5                   10

<210> SEQ ID NO 23
<211> LENGTH: 13
<212> TYPE: PRT
<213> ORGANISM: Rat

<400> SEQUENCE: 23

Arg Glu Pro Gly Val Ala Asn Pro Arg Arg Asp Ala Gly
1               5                   10

<210> SEQ ID NO 24
<211> LENGTH: 13
<212> TYPE: PRT
<213> ORGANISM: Guinea Pig

<400> SEQUENCE: 24

Arg Leu Pro Gly Leu Gly Asn Pro Arg Arg Glu Ala Gly
1               5                   10

<210> SEQ ID NO 25
<211> LENGTH: 13
<212> TYPE: PRT
<213> ORGANISM: Bos Taurus

<400> SEQUENCE: 25

Arg Glu Pro Gly Leu Gly Asn Pro Arg Arg Glu Ala Ser
1               5                   10
```

```
<210> SEQ ID NO 26
<211> LENGTH: 13
<212> TYPE: PRT
<213> ORGANISM: Pig

<400> SEQUENCE: 26

Arg Glu Pro Gly Leu Gly Asn Pro Arg Arg Glu Ala Gly
1               5                   10
```

ALPHA-2A-ADRENERGIC RECEPTOR POLYMORPHISMS

The present application is a divisional application of U.S. application Ser. No. 09/636,259 filed Aug. 10, 2000 now abandoned.

This invention was made, in part, with government support by National Institutes of Health grants ES06096, and HL41496. The U.S. Government may have certain rights in this invention.

Throughout this application, various references are referred to. Disclosures of these publications in their entireties are hereby incorporated by reference into this application to describe more fully the state of the art to which this invention pertains.

FIELD OF THE INVENTION

The invention relates to a polymorphism in the gene encoding an alpha adrenergic receptor subtype. Such a polymorphism result in altered alpha-adrenergic receptor function and can cause or modify a disease and/or alter the response to pharmacologic treatment. More specifically, the present invention relates to specific polymorphisms in the alpha-2A adrenergic receptor gene and polymorphisms in the expressed alpha-2A adrenergic receptor. The invention further relates to methods and molecules for identifying one or more polymorphisms in the alpha-2A adrenergic receptor gene and alpha-2A adrenergic receptor, methods of diagnosing, prognosing and treating individuals with diseases associated with one or more polymorphisms in the alpha-2A adrenergic receptor.

BACKGROUND OF THE INVENTION

Alpha adrenergic receptors are plasma membrane receptors which are located in the peripheral and central nervous systems throughout the body. They are members of a diverse family of structurally related receptors which contain seven putative helical domains and transduce signals by coupling to guanine nucleotide binding proteins (G-proteins).

The alpha adrenergic receptor family of adrenergic receptors (AR) consists of two groups: alpha-1 and alpha-2. Of the alpha-2 group, there are three distinct subtypes denoted alpha-2A, alpha-2B and alpha-2C. The subtypes are derived from different genes, have different structures, unique distributions in the body, and specific pharmacologic properties. (Due to localization of the genes to human chromosomes 10, 2 and 4, the alpha-2A, alpha-2B, and alpha-2C receptors have sometimes been referred to as alpha-2C10, alpha-2C2 and alpha-2C4 receptors, respectively). Like other adrenergic receptors, the alpha-2 receptors are activated by endogenous agonists such as epinephrine (adrenaline) and norepinephrine (noradrenaline), and synthetic agonists, which promotes coupling to G-proteins that in turn alter effectors such as enzymes or channels.

The alpha-2 receptors couple to the $G_i$ and $G_o$ family of G-proteins. Alpha-2 receptors modulate a number of effector pathways in the cell: inhibition of adenylyl cyclase (decreases cAMP), stimulation of mitogen activated protein (MAP) kinase, stimulation of inositol phosphate accumulation, inhibition of voltage gated calcium channels and opening of potassium channels. (Limbird, L. E. (1988) *FASEB J*2, 2686–2695, Luttrell, L. M., van Biesen, T., Hawes, B. E., Della Rocca, G. J., and Luttrell, D. K., and Lefkowitz, R. J. (1998) in *Catecholamines: Bridging Basic Science with Clinical Medicine* (Goldstein, D. S., Eisenhofer, G., and McCarty, R., eds pp. 466–470, Academic Press). The alpha-2 receptors are expressed on many cell-types in multiple organs in the body including those of the central and peripheral nervous systems. They are found in presynaptic or postsynaptic locations with the alpha 2AR being the most extensively expressed of the subtypes.

Alpha-2AAR are the principal presynaptic inhibitory autoreceptors of central and peripheral sympathetic nerves and inhibit neurotransmitter release in the brain and cardiac sympathetic nerves. (Hein, L., Altman, J. D., and Kobilka, B. K. (1999) *Nature* 402, 181–184). Such inhibition of neurotransmitter release in the brain is the basis for the central hypotensive, sedative, anesthetic-sparing, and analgesic responses of alpha-2AAR agonists (Altman, J. D., Trendelenburg, A. U., MacMillan, L., Bernstein, D., Limbird, L., Starke, K., Kobilka, B. K., and Hein, L. (1999) *Mol. Pharmacol.* 56, 154–161 and Lakhlani, P. P., MacMillan, L. B., Guo, T. Z., McCool, B. A., Lovinger, D. M., Maze, M., and Limbird, L. E. (1997) *Proc Natl Acad Sci USA* 94, 9950–9955). Indeed, alpha-2AAR agonists such as clonidine and guanabenz are potent antihypertensive agents which act via central presynaptic alpha-2AAR (Holmes, B., Brogden, R. N., Heel, R. C., Speight, T. M., and Avery, G. S. (1983) *Drugs* 26, 212–229). The blood pressure and other responses to alpha-2AAR agonists and antagonists, though, are subject to interindividual variation in the human population (Holmes, B., Brogden, R. N., Heel, R. C., Speight, T. M., and Avery, G. S. (1983) *Drugs* 26, 212–229; Dao, T. T., Kailasam, M. T., Parmer, R. J., Le, H. V., Le Verge, R., Kennedy, B. P., Ziegler, G., Insel, P. A., Wright, F. A., and O'Connor, D. T. (1998) *J Hypertens* 16, 779–792; Goldstein, D. S., Grossman, E., Listwak, S., and Folio, C. J. (1991) *Hypertension* 18, III40–III48). Such variation, of course, can be due to genetic variation in the structure of the receptor itself, its cognate G-proteins, the effectors, or downstream intracellular targets.

Of particular interest are physiologic and genetic studies which suggest that altered alpha-2AAR function can predispose individuals to essential hypertension (Holmes, B., Brogden, R. N., Heel, R. C., Speight, T. M., and Avery, G. S. (1983) *Drugs* 26, 212–229; Dao, T. T.; Kailasam, M. T., Parmer, R. J., Le, H. V., Le Verge, R., Kennedy, B. P., Ziegler, G., Insel, P. A., Wright, F. A., and O'Connor, D. T. (1998) *J Hypertens* 16, 779–792; Goldstein, D. S., Grossman, E., Listwak, S., and Folio, C. J. (1991) *Hypertension* 18, III40–III48). Other physiologic functions of the alpha-2AAR are known. For example, the alpha-2AAR act to inhibit insulin secretion by pancreatic beta-cells, contract vascular smooth muscle, inhibit lipolysis in adipocytes, modulate water and electrolyte flux in renal cells, and aggregate platelets (Ruffolo, R. R., Jr., Nichols, A. J., Stadel, J. M., and Hieble, J. P. (1993) *Annu Rev Pharmacol Toxicol* 32, 243–279). Thus, like what has been shown with beta-AR polymorphisms (Liggett, S. B. (1998) *Clin and Exp. Allergy* 28, 77–79), potential polymorphisms of the alpha-2AAR may act as risk factors for disease, act to modify a given disease, or alter the therapeutic response to agonists or antagonists.

There has been a considerable research effort to clone and sequence the alpha-2AR. For example, the gene encoding the alpha-2A, alpha-2B, alpha-2C subtypes has been cloned and sequenced. (Kobilka et al. *Science* 238, 650–656 (1987); Regan et al., Lomasney et al. *Proc. Nat. Acad. Sci.* 87, 5094–5098 (1994)). These receptors have also been named as alpha-2C10, alpha-2C2 and alpha-2C4, according to their location on chromosomes 10, 4 and 2.

Polymorphisms near the coding regions in the alpha-2A, alpha-2C and dopamine β-hydroxylase (DBH) genes have been reported causing increased levels of norepinephrine in children with attention-deficit hyperactivity disorder (Comings et al. *Clin Genet* 55, 160–172 (1999)). Indeed, there have been several reports of non-coding region polymorphisms (i.e., in the 5' and 3' untranslated region) of the human alpha-2A AR. One report has identified three SNPs in the coding region (Feng et al. *Am. J. Med. Genet. (Neuropsychiatr. Genet.)* 81, 405–410 (1998). In this work, though, no pharmacologic studies were carried out to determine if these polymorphisms alter receptor function.

Given the importance of the alpha-2AAR in modulating a variety of physiological functions, there is a need in the art for improved methods to identify polymorphisms and to correlate the identity of these polymorphisms with signaling functions of alpha-2AAR. The present invention addresses these needs and more by providing nucleic acid and amino acid polymorphisms, molecules, and methods for identifying the polymorphisms in the alpha-2AAR. The present invention is useful for determining an individual's risk for developing a disease, assist the clinician in diagnosing and prognosing the disease. The present invention also provides methods for selecting appropriate drug treatment based on the identity of such polymorphism.

SUMMARY OF THE INVENTION

The present invention is directed to molecules useful for determining the identity of one or more polymorphic sites in nucleic acids encoding the alpha-2A adrenergic receptor gene and gene products.

In one embodiment, the present invention provides an isolated polynucleotide encoding an alpha-2A adrenergic receptor molecule comprising SEQ ID NO: 1 or 2 or fragment or complement thereof, wherein the polynucleotide comprises at least one polymorphic site.

In a second embodiment, the present invention provides an isolated alpha-2A adrenergic receptor gene product comprising SEQ ID NO: 3 or 4 or fragment thereof, wherein the gene product comprises at least one polymorphic site.

In a third embodiment, the present invention provides an oligonucleotide comprising from about 10 to about 50 nucleotides that hybridize with a region upstream of nucleotide position 753 of SEQ ID NO: 1 or 2 or complementary sequence thereof, and wherein the oligonucleotide does not hybridize with nucleotide position 753 of SEQ ID NO: 1 or 2 or complementary sequence thereof.

In another embodiment, the present invention provides an oligonucleotide comprising from about 10 to about 50 nucleotides that hybridize with a region downstream of nucleotide position 753 of SEQ ID NO: 1 or 2 or complementary sequence thereof, and wherein the oligonucleotide does not hybridize with nucleotide position 753 of SEQ ID NO: 1 or 2 or complementary sequence thereof.

In still yet another embodiment, the present invention provides an oligonucleotide comprising a nucleotide sequence complementary to a region of SEQ ID NO: 1 or 2 or fragment thereof that encode an alpha-2A adrenergic receptor molecule and which, when hybridized to the region permit identification of at least one polymorphic site.

In a particular embodiment, the present invention provides a primer oligonucleotide for polymerase-mediated extension comprising at least one polymorphic site of SEQ ID NO: 1 or 2, wherein polymerase-mediated extension of the primer amplifies the polymorphic site.

In another particular embodiment, the present invention provides a kit for detecting at least one polymorphism in nucleic acids encoding an alpha-2A adrenergic receptor molecule comprising a container having an oligonucleotide comprising a region of SEQ ID NO: 1 or 2 or complement thereof for detecting the polymorphism.

In still yet another particular embodiment, the present invention provides a kit for detecting at least one polymorphism in nucleic acids encoding an alpha-2A adrenergic receptor molecule comprising a container having at least two primers for amplifying SEQ ID NO: 1 or 2 or fragment or complement thereof and at least one detection primer for detecting the polymorphism.

In one exemplary embodiment, the present invention provides a method of genotyping nucleic acids encoding an alpha-2A adrenergic receptor molecule from a sample comprising performing a primer extension reaction employing an oligonucleotide comprising a region of SEQ ID NO: 1 or 2 or complement thereof.

In a second exemplary embodiment, the present invention provides a method of genotyping nucleic acids encoding an alpha-2A adrenergic receptor molecule from a sample of an individual, comprising: a) isolating from the individual the sample having a polynucleotide encoding the alpha-2A adrenergic receptor molecule comprising SEQ ID NO: 1 or 2 or fragment or complement thereof, b) incubating the polynucleotide with at least one oligonucleotide, the oligonucleotide having a nucleotide sequence that is complementary to a region of the polynucleotide, and which, when hybridized to the region permits the identification of the nucleotide present at a polymorphic site of the polynucleotide, wherein the incubation is under conditions sufficient to allow specific hybridization to occur between complementary nucleic acid molecules; c) permitting the hybridization to occur; and d) identifying the polymorphic site to obtain the genotype of the individual.

In another exemplary embodiment, the present invention provides a method for determining an individual at increased risk for developing a disease associated with an alpha-2A adrenergic receptor molecule which comprises obtaining a sample comprising nucleic acids from the individual and detecting a polymorphism in nucleic acids encoding the alpha-2A adrenergic receptor molecule comprising SEQ ID NO: 1 or 2 or fragment or complement thereof which correlates to the disease thereby identifying the individual at increased risk for the disease.

In still yet another exemplary embodiment, the present invention provides a method for diagnosing or prognosing an individual with a disease associated with an alpha-2A adrenergic receptor molecule, comprising obtaining a sample comprising nucleic acids from the individual and detecting a polymorphism in nucleic acids encoding the alpha-2A adrenergic receptor molecule comprising SEQ ID NO: 1 or 2 or fragment or complement thereof which correlates to the disease thereby diagnosing or prognosing the disease.

One advantage of the present invention is to provide a method of predicting an individual's response to an agonist or antagonist, comprising: a) obtaining a sample comprising nucleic acids from the individual; b) detecting a polymorphism in the nucleic acids encoding the alpha-2A adrenergic receptor molecule comprising SEQ ID NO: 1 or 2 or fragment or complement thereof; and iii) correlating the polymorphism to a predetermined response thereby predicting the individual's response to the agonist or antagonist.

A second advantage of the present invention is to provide a method for selecting an appropriate pharmaceutical composition to administer to an individual having a disease associated with an alpha-2A adrenergic receptor molecule comprising detecting in a sample a polymorphism in nucleic acids encoding the alpha-2A adrenergic receptor molecule comprising SEQ ID NO: 1 or 2 or fragment or complement thereof in the individual and selecting the appropriate pharmaceutical composition based on the polymorphism present.

A third advantage of the present invention is to provide recombinant host cells, and expression vectors having a polynucleotide encoding the alpha-2A adrenergic receptor molecule comprising SEQ ID NO: 2.

Another advantage of the present invention is to provide a transgenic animal having incorporated into its genome a polynucleotide comprising SEQ ID NO: 2.

Yet another advantage of the present invention is to provide an isolated antibody that binds with an epitope on SEQ ID NO: 4 or fragment thereof.

For a better understanding of the present invention together with other and further advantages and embodiments, reference is made to the following description taken in conjunction with the examples, the scope of which is set forth in the appended claims.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying figures, wherein:

FIG. 2 illustrates the location of the Lys251 alpha-2AAR polymorphism and alignment of flanking amino acid residues of the third intracellular loop from various species. The locations of the Lys251 amino acid polymorphism in the third intracellular loop as well as two synonymous SNPs (single nucleotide polymorphisms) are indicated. Alignment of alpha-2AAR amino acid sequence from various species shows that this region is highly conserved and that Asn at position 251 is invariant in all mammalian species reported to date except for humans where we have noted the Lys polymorphism. Amino acids in the mid-portion of the third intracellular loop are represented as solid dots for convenience.

DETAILED DESCRIPTION OF THE INVENTION

Alpha-2A Adrenergic Receptor Function

Figure 1A:
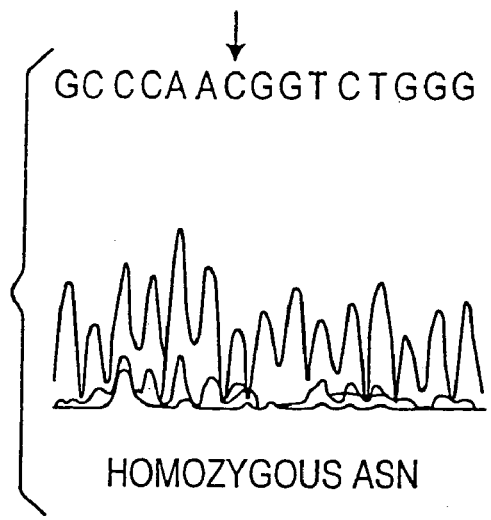
FIG. 1 illustrates sequence variation of the human alpha-2AAR at nucleotide position 753. Shown are sequence electropherograms (sense strand) of PCR products amplified from individuals homozygous for the wild-type alpha-2AAR and Lys251 receptor (Panels A and B), and a heterozygous individual (Panel C) as described below. The cytosine in the indicated position of codon 251 results in an Asn, whereas a guanine encodes for Lys. Panel D shows agarose gel of PCR products from homozygous wild-type (Asn), heterozygous (Asn/Lys), and homozygous polymorphic (Lys) individuals digested with Sty I. The C to G transversion at nucleotide 753 creates a unique Sty I site that results in partial and complete digestion of a 556 bp fragment amplified from Lys251 heterozygous and homozygous individuals, respectively.

The alpha-2A adrenergic receptor is localized at the cell membrane and serves as a receptor for the endogenous catecholamine agonists i.e., epinephrine and norepinephrine, and synthetic agonists and antagonists. Upon binding of the agonist, the receptor stabilizes in a conformation that favors contact with all activation of certain heterotrimeric G proteins. These include $G_{i1}$, $G_{i2}$, $G_{i3}$ and $G_o$. The $G_i$ G protein alpha subunits serve to decrease the activity of the enzyme adenylyl cyclase, which lowers the intracellular levels of cAMP (a classic second messenger). The alpha subunits, and/or the beta-gamma subunits of these G proteins also act to activate MAP kinase, open potassium channels, inhibit voltage gated calcium channels, and stimulate inositol phosphate accumulation. The physiologic consequences of the initiation of these events include inhibition of neurotransmitter release from central and peripheral noradrenergic neurons. Since most organs have innervation by these neurons, the alpha-2A receptor activity can alter processes in many organ systems. The alpha-2A has been localized in brain, blood vessels, heart, lung, skeletal muscle, pancreas, kidney, prostate, ileum, jejunum, spleen, adrenal gland and spinal cord (Eason et al. Molecular Pharmacology 44, 70–75 (1993); Zeng et al. Mol Brain Res 10, 219–225 (1991). Of particular therapeutic interest has been the development of highly subtype-specific alpha-2 agonists and antagonists. Such compounds, then, can selectively block or activate one subtype, such as the alpha-2A, without affecting the others. This would provide for highly specific responses without side-effects from activating the other subtypes.

Alpha-2AARs are widely expressed and participate in a broad spectrum of physiologic functions including metabolic, cardiac, vascular, and central and peripheral nervous systems, via pre-synaptic and post-synaptic mechanisms. At peripheral sites, alpha-2AARs act to inhibit insulin secretion by pancreatic beta-cells, contract vascular smooth muscle, inhibit lipolysis in adipocytes, modulate water and electrolyte flux in renal cells, and aggregate platelets (Ruffolo, R. R., Jr., Nichols, A. J., Stadel, J. M., and Hieble, J. P. (1993) *Annu Rev Pharmacol Toxicol* 32, 243–279). As discussed above, the alpha-2AAR is the principal presynaptic inhibitory autoreceptor of central and peripheral sympathetic nerves (Hein, L., Altman, J. D., and Kobilka, B. K. (1999) *Nature* 402, 181–184). Such inhibition of neurotransmitter release in the brain is the basis for the central hypotensive, sedative, anesthetic-sparing, and analgesic responses of alpha-2AAR agonists (Altman, J. D., Trendelenburg, A. U., MacMillan, L., Bernstein, D., Limbird, L., Starke, K., Kobilka, B. K., and Hein, L. (1999) *Mol. Pharmacol.* 56, 154–161 and Lakhlani, P. P., MacMillan, L. B., Guo, T. Z., McCool, B. A., Lovinger, D. M., Maze, M., and Limbird, L. E. (1997) *Proc Natl Acad Sci USA* 94, 9950–9955).

Alpha-2AAR agonists such as clonidine and guanabenz are potent antihypertensive agents which act via central presynaptic alpha-2AARs (Holmes, B., Brogden, R. N., Heel, R. C., Speight, T. M., and Avery, G. S. (1983) *Drugs* 26, 212–229). The blood pressure and other responses to alpha-2AAR agonists and antagonists, though, are subject to interindividual variation in the human population ( Holmes, B., Brogden, R. N., Heel, R. C., Speight, T. M., and Avery, G. S. (1983) *Drugs* 26, 212–229; Dao, T. T., Kailasam, M. T., Parmer, R. J., Le, H. V., Le Verge, R., Kennedy, B. P., Ziegler, G., Insel, P. A., Wright, F. A., and O'Connor, D. T. (1998) *J Hypertens* 16, 779–792; Goldstein, D. S., Grossman, E., Listwak, S., and Folio, C. J. (1991) *Hypertension* 18, III40–III48). Such variation can be due to genetic variation in the structure of the receptor itself, its cognate G-proteins, the effectors, or downstream intracellular targets. Of particular interest are physiologic and genetic studies which suggest that altered alpha-2AAR function can predispose individuals to essential hypertension. See for example, (Holmes, B., Brogden, R. N., Heel, R. C., Speight, T. M., and Avery, G. S. (1983) *Drugs* 26, 212–229; Dao, T. T., Kailasam, M. T., Parmer, R. J., Le, H. V., Le Verge, R., Kennedy, B. P., Ziegler, G., Insel, P. A., Wright, F. A., and O'Connor, D. T. (1998) *J Hypertens* 16, 779–792; Goldstein, D. S., Grossman, E., Listwak, S., and Folio, C. J. (1991) *Hypertension* 18, III40–III48) (Lockette, W., Ghosh, S., Farrow, S., MacKenzie, S., Baker, S., Miles, P., Schork, A., and Cadaret, L. (1995) *Am J Hypertens* 8, 390–394 and Svetkey, L. P., Timmons, P. Z., Emovon, O., Anderson, N. B., Preis, L., and Chen, Y.-T. (1996) *Hypertension* 27, 1210–1215). Thus, like what has been shown with beta-AR polymorphisms (Liggett, S. B. (1998) *Clin and Exp. Allergy* 28, 77–79), potential polymorphisms of the alpha-2AAR can act as risk factors for disease, act to modify a given disease, or alter the therapeutic response to agonists or antagonists.

Alpha-2A Adrenergic Receptor Diseases

Alpha-adrenergic receptors play an important role in regulating a variety of physiological functions because of their distribution in many organs of the body and the brain. Thus, dysfunctional alpha-2A receptors can predispose to, or modify, a number of diseases or alter response to therapy. The present invention stems in part from the recognition that certain polymorphisms in the alpha-2AAR result in receptor molecules with altered functions. These altered functions put an individual at risk for developing diseases associated with the alpha-2AAR. Such diseases include cardiovascular diseases such as hypertension, hypotension, congestive heart failure, arrhythmias, stroke, myocardial infarction, neurogenic and obstructive peripheral vascular disease, ischemia-reperfusion damage and intermittent claudication, migraine, and combinations thereof. Central nervous systems (CNS) diseases are also contemplated by the present invention. Some examples of CNS diseases include Parkinsonism, Alzheimers, attention deficit disorder, hyperreactivity, anxiety, manic-depression and combinations thereof. Since the alpha-2A controls certain central nervous system and peripheral functions as discussed above, dysfunctional polymorphisms are likely to be important in as of yet unclassified disorders of memory and behavior.

In one embodiment, the present invention includes methods of determining the risk an individual has for developing a disease. Alternatively, the present invention can be used to diagnose or prognose an individual with a disease. For example, a polymorphic site in SEQ ID NO: 1, such as for example, nucleotide position 753 can be detected. This polymorphic site corresponds to a cytosine in nucleic acids encoding the alpha-2AAR. This exemplified polymorphism results in asparagine at amino acid position 251 of SEQ ID NO: 3 of the alpha-2A adrenergic receptor molecule resulting in a receptor with decreased alpha-agonist function. Such polymorphism can be correlated to increasing an individual's risk for developing a disease, or can be used to determine a diagnosis or prognosis for the disease.

In another embodiment of the present invention, a polymorphic site in SEQ ID NO: 2, such as for example, nucleotide position 753 can be detected. This polymorphic site corresponds to a guanine in nucleic acids encoding the alpha-2AAR. This exemplified polymorphism results in lysine at amino acid position 251 of SEQ ID NO:4 of the alpha-2A adrenergic receptor molecule resulting in a receptor with increased alpha-agonist function. Such polymorphism can be correlated to increasing an individual's risk for developing a disease, or can be used to determine a diagnosis or prognosis for the disease.

As used herein, "diagnosis" includes determining the nature and cause of the disease, based on signs and symptoms of the disease and laboratory finding. One such laboratory finding is the identification of at least one polymorphism in nucleic acids encoding the alpha-2AAR. Prognosis of a disease includes determining the probable clinical course and outcome of the disease. Increased risk for the disease includes an individual's propensity or probability for developing the disease.

The terms "correlating the polymorphism with a disease" includes associating the polymorphism which occurs at a higher allelic frequency or rate in individuals with the disease than individuals without the disease. Correlation of the disease with the polymorphism can be accomplished by bio-statistical methods known in the art, such as for example, by Chi-squared tests or other methods described by L. D. Fisher and G. vanBelle, *Biostatistics: A Methodology for the Health Sciences*, Wiley-Interscience (New York) 1993.

Preferably, the identity of at least one polymorphic site in an alpha-2A adrenergic receptor molecule is determined. Generally, in performing the methods of the present invention, the identity of more than one polymorphic site is determined. As used herein a polymorphic site includes one or more nucleotide deletions, insertions, or base changes at a particular site in a nucleic acid sequence. In some preferred embodiments, the identity of between about two and about six polymorphic sites are determined, though the identification of other numbers of sites is also possible. Most preferably, the polymorphisms and molecules of the present invention are utilized in determining the identity of at least one polymorphic site of the alpha-2AAR molecule and using that identity as a predictor of increased risk for developing a disease. The type of polymorphism present can also dictate the appropriate drug selection. In other embodiments, the polymorphisms and molecules of the present are used for diagnosing or prognosing an individual with a disease associated with an alpha-2AAR molecule.

Alpha-2A Adrenergic Receptor Polymorphisms

The particular gene sequences of interest to the present invention comprise "mutations" or "polymorphisms" in the genes encoding the alpha-2A adrenergic receptor.

The genomes of animals and plants naturally undergo spontaneous mutation in the course of their continuing evolution (J. F. Gusella *Ann. Rev. Biochem.* 55:831–854 (1986)). These mutations may be in the form of deletions, insertions, or base changes at a particular site in a nucleic acid sequence. This altered sequence and the initial sequence may co-exist in a species' population. In some instances, these changes confer neither an advantage or a disadvantage to the species and multiple alleles of the sequence may be in stable or quasi-stable equilibrium. In some instances, however, these sequence changes will confer a survival or evolutionary advantage to the species, and accordingly, the altered allele may eventually (i.e. over evolutionary time) be incorporated into the genome of many or most members of that species. In other instances, the altered sequence confers a disadvantage to the species, as where the mutation causes or predisposes an individual to a genetic disease. As used herein, the terms "mutation" or "polymorphism" refer to the condition in which there is a variation in the DNA sequence between some members of a species. Typically, the term "mutation" is used to denote a variation that is uncommon (less than 1%), a cause of a rare disease, and that results in a gene that encodes a non-functioning protein or a protein with a substantially altered or reduced function. Such mutations or polymorphisms include, but are not limited to, single nucleotide polymorphisms (SNPs), base deletions, and base insertions. Such mutations and polymorphisms may be either heterozygous or homozygous within an individual. Homozygous individuals have identical alleles at one or more corresponding loci on homologous chromosomes. While heterozygous individuals have two different alleles at one or more corresponding loci on homologous chromosomes.

A polymorphism is thus said to be "allelic," in that, due to the existence of the polymorphism, some members of a species carry a gene with one sequence (e.g., the original or wild-type "allele"), whereas other members may have an altered sequence (e.g.; the variant or, mutant "allele"). In the simplest case, only one mutated variant of the sequence may exist, and the polymorphism is said to be diallelic. The occurrence of alternative mutations can give rise to triallelic and tetra-allelic polymorphisms, etc. An allele may be referred to by the nucleotide(s) that comprise the mutation.

The wild-type gene encoding the third intracellular loop of the human alpha-2A receptor molecule is disclosed in GenBank Accession No. AF281308 which include the sequence corrections illuminated by Guyer, C. A., Horstman, D. A., Wilson, A. L., Clark, J. D., Cragoe, E. J. Jr., and Limbird, L. E. (1990) *J Biol Chem* 265, 17307–17317, both references are herein incorporated by reference. The terms "alpha-2A-adrenergic receptor polymorphism" or "alpha-2AAR polymorphism", are terms of art and refer to at least one polymorphism in the nucleic acid or amino acid sequence of an alpha-2A adrenergic receptor gene or gene product.

For purposes of the present application, the wild-type gene encoding the alpha-2A-adrenergic receptor is designated SEQ ID NO: 1 and the wild-type gene product comprising the alpha-2A-adrenergic receptor molecule, is designated amino acid SEQ ID NO:3.

Those in the art will readily recognize that nucleic acid molecules may be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense) strand of a nucleic acid molecule is also intended to include the thymine (uridine), adenine, guanine, or cytosine (respectively) at the corresponding site on a minus (antisense) strand of a complementary strand of a nucleic acid molecule. Thus, reference may be made to either strand and still comprise the same polymorphic site and an oligonucleotide may be designed to hybridize to either strand. Throughout this specification, in identifying a polymorphic site, reference is made to the sense strand, only for the purpose of convenience.

Preferred polymorphisms of the present invention occur in the gene encoding for the alpha-2A adrenergic receptor molecule identified as SEQ ID No: 1 or 2 or fragments thereof or complements thereof.

For the purposes of identifying the location of at least one polymorphism or polymorphic site, the first nucleotide of the start codon of the coding region (the adenine of the ATG in a DNA molecule and the adenine of the AUG in an RNA molecule) of the alpha-2AAR gene is considered nucleotide "1." This corresponds to nucleotide 1 of SEQ ID NO:1 or 2. The end of the coding region corresponds to guanine at position 1350 of SEQ ID NO:1 or 2. According to the present invention, polymorphisms can occur any where in the coding region identified as SEQ ID NO:1 or 2.

Preferred single nucleotide polymorphisms and polymorphic sites occurring in the alpha-2AAR gene and the encoded protein or gene product include the following:

TABLE A

| Type | Nucleotide Position | Nucleotide | Amino Acid position | Designation |
|---|---|---|---|---|
| Wild Type | 753 o SEQ ID NO: 1 | C | 251 of SEQ ID NO: 3 | Asn 251 |
| Mutant | 753 of SEQ ID NO: 2 | G | 251 of SEQ ID NO: 4 | Lys 251 |

Figure 1B:
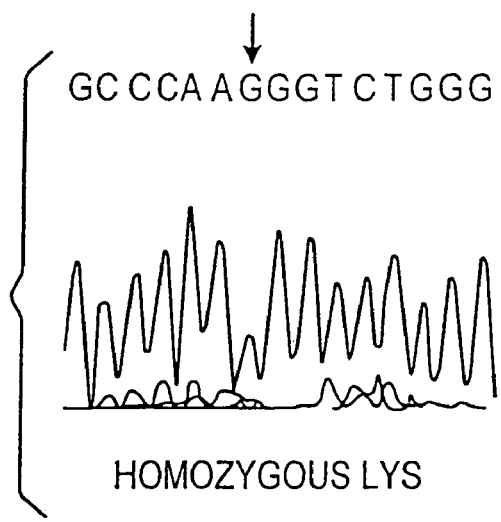
Figure 1C:
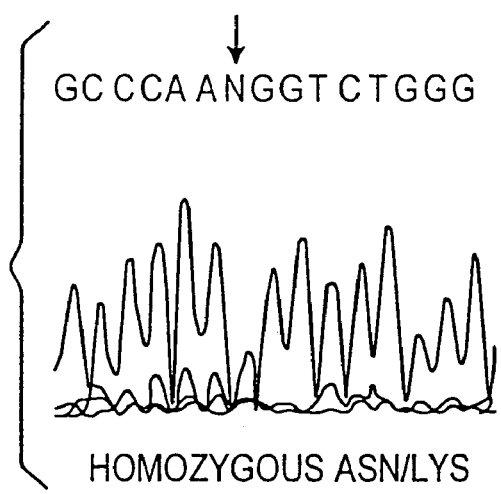
Figure 1D:
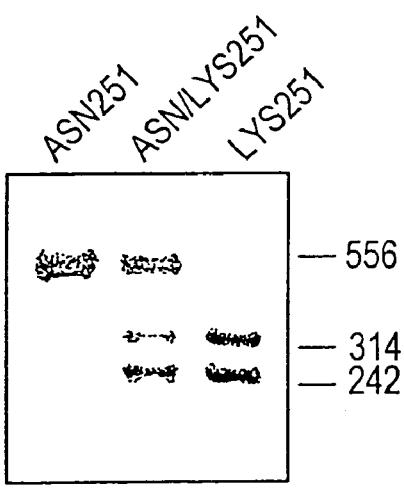

In one embodiment of the present invention, Applicants have discovered at least one polymorphic site on SEQ ID NO: 1 that encodes the wild-type alpha-2AAR molecule (Table A). Such polymorphic site corresponds to C at nucleotide position 753 of SEQ ID NO: 1 in the coding region of the alpha-2AAR molecule (FIG. 1B). This SNP is localized within an intracellular domain of the alpha-2AAR molecule.

In another embodiment of the present invention at least one polymorphic site has been identified in SEQ ID NO: 2 that encodes the mutant alpha-2AAR molecule (Table A). Such polymorphic site corresponds to G at nucleotide position 753 of SEQ ID NO: 2 in the coding region for the alpha-2AAR molecule (FIG. 1A). This SNP is localized within an intracellular domain of the alpha-2AAR molecule.

The polymorphisms of the present invention can occur in the translated alpha-2A adrenergic receptor molecule as well. For example, the first amino acid of the translated protein product or gene product (the methionine) is considered amino acid "1" in the wild-type or mutant alpha-2A adrenergic receptor molecule designated amino acid SEQ ID NO: 3 or 4, respectively. Polymorphisms can occur anywhere in SEQ ID NO: 3 or 4. The wild-type alpha-2A adrenergic receptor molecule (FIG. 2) comprises N at amino acid position 251 (Asn 251) of the alpha-2A adrenergic receptor molecule. Accordingly, amino acid position 251 is a polymorphic site (Table A).

In another embodiment of the present invention, SEQ ID NO:4 is the entire mutant amino acid sequence of alpha-2A adrenergic receptor molecule. Polymorphisms can occur anywhere in the amino acid sequence designated SEQ ID NO:4. For example, the mutant alpha-2A adrenergic receptor molecule comprises G at amino acid position 251 (Lys 251) of the alpha-2A adrenergic receptor. Accordingly, amino acid position 251 is a polymorphic site (Table A).

As used herein "fragments" include less than the entire nucleotide sequence of SEQ ID NO:1 or 2. In order for a nucleic acid sequence to be a fragment, it must be readily identifiable by the molecular techniques as discussed below, such as with nucleic acid probes. Preferred gene product fragments include less than the entire amino acid sequence of SEQ ID NO: 3 or 4. In order for an amino acid sequence to be a fragment, it must be readily identifiable by molecular and pharmacological techniques as discussed below, such as with ligand binding.

Alpha-2A Adrenergic Receptor Molecules

The molecules of the present invention are particularly relevant to determine increased risk an individual has for a disease and/or response to therapy. The molecules of the present invention can also be used to diagnosis and prognosis a disease.

The molecules of the present invention will preferably be "biologically active" with respect to either a structural attribute, such as the capacity of a nucleic acid to hybridize to another nucleic acid molecule or to be used by a polymerase as a primer. Alternatively, such an attribute may be catalytic, and thus involve the capacity of the agent to mediate a chemical reaction or response.

A preferred class of molecules of the present invention comprise adrenergic receptor molecules. Preferably, alpha-2A-adrenergic receptor molecules. Such molecules may be either DNA or RNA, single-stranded or double-stranded. Alternatively, such molecules may be proteins and antibodies. Such molecules may also be fragments, portions, and segments thereof and molecules, such as oligonucleotides, that specifically hybridize to nucleic acid molecules encoding the alpha-2A-adrenergic receptor. Such molecules may be isolated, derived, or amplified from a biological sample. Alternatively, the molecules of the present invention may be chemically synthesized. The term "isolated" as used herein refers to the state of being substantially free of other material such as nucleic acids, proteins, lipids, carbohydrates, or other materials such as cellular debris or growth media with which the alpha-2A-adrenergic receptor molecule, target polynucleotide, primer oligonucleotide, or allele-specific oligonucleotide may be associated. Typically, the term "isolated" is not intended to refer to a complete absence of these materials. Neither is the term "isolated" generally intended to refer to water, buffers, or salts, unless they are present in amounts that substantially interfere with the methods of the present invention. The term "sample" as used herein generally refers to any material containing nucleic acid, either DNA or RNA. Generally, such material will be in the form of a blood sample, tissue sample, cells, bacteria, histology section, or buccal swab, either fresh, fixed, frozen, or embedded in paraffin.

As used herein, the term "polynucleotide" includes nucleotides of any number. Preferred polynucleotides include SEQ ID NO:1 or 2 and complements and fragments thereof. The term "oligonucleotide" as used herein includes a polynucleotide molecule comprised of any number of nucleotides, preferably, less than about 200 nucleotides. More preferably, oligonucleotides are between 5 and 100 nucleotides in length. Most preferably, oligonucleotides are 10 to 50 nucleotides in length. The exact length of a particular oligonucleotide, however, will depend on many factors, which in turn depend on the ultimate function or use of the oligonucleotide. Short primer molecules generally require lower temperatures to form sufficiently stable hybrid complexes with the template. Preferred oligonucleotides of the present invention include: 5'-TTTACCCATCGGCTCTC-CCTAC-3' (SEQ ID NO: 5); 5'GAGACACCAGGAAGAG-GTTTTGG-3' (SEQ ID NO: 6); 5'-TCGTCATCATCGC-CGTGTTC-3' (SEQ ID NO: 7); 5'-CGTACCACTTCTGGTCGTTGATC-3' (SEQ ID NO: 8); 5'-GCCATCATCATCACCGTGTGGGTC-3' (SEQ ID NO: 9); 5'-GGCTCGCTCGGGCCTTGCCTTTG-3' (SEQ ID NO: 10); 5'-GACCTGGAGGAGAGCTCGTCTT-3' (SEQ ID NO: 11); 5'-TGACCGGGTTCAACGAGCT-GTTG-3' (SEQ ID NO: 12); 5'-GCCACGCACGCTCT-TCAAATTCT-3' (SEQ ID NO: 13); 5'-TTCCCTTGTAG-GAGCAGCAGAC-3' (SEQ ID NO: 14); 5'-TGTAAAACGACGGCCAGT-3' (SEQ ID NO: 15); 5'-CAGGAAACAGCTATGACC-3' (SEQ ID NO: 16) and complementary sequences thereof.

Oligonucleotides, such as primer oligonucleotides are preferably single stranded, but may alternatively be double stranded. If double stranded, the oligonucleotide is generally first treated to separate its strands before being used for hybridization purposes or being used to prepare extension products. Preferably, the oligonucleotide is an oligodeoxyribonucleotide. Oligonucleotides may be synthesized chemically by any suitable means known in the art or derived from a biological sample, as for example, by restriction digestion. The source of the oligonucleotides is not essential to the present invention. Oligonucleotides may be labeled, according to any technique known in the art, such as with radiolabels, fluorescent labels, enzymatic labels, proteins, haptens, antibodies, sequence tags, etc. The term "nucleotide" or nucleic acid as used herein is intended to refer to ribonucleotides, deoxyribonucleotides, acylic derivatives of nucleotides, and functional equivalents thereof, of any phosphorylation state. Functional equivalents of nucleotides are those that act as substrates for a polymerase as, for example, in an amplification method. Functional equivalents of nucleotides are also those that may be formed into a polynucleotide that retains the ability to hybridize in a sequence specific manner to a target polynucleotide.

Such oligonucleotides may be used as probes of a nucleic acid sample, such as genomic DNA, mRNA, or other suitable sources of nucleic acid. For such purposes, the oligonucleotides must be capable of specifically hybridizing to a target polynucleotide or DNA nucleic acid molecule. As used herein, two nucleic acid molecules are said to be capable of specifically hybridizing to one another if the two molecules are capable of forming an anti-parallel, double-stranded nucleic acid structure under hybridizing conditions, whereas they are substantially unable to form a double-stranded structure when incubated with a non-alpha-2AAR nucleic acid molecule under the same conditions. A nucleic acid molecule is said to be the "complement" of another nucleic acid molecule if it exhibits complete complementarity. As used herein, molecules are said to exhibit "complete complementarity" when every nucleotide of one of the molecules is complementary to a nucleotide of the other. Two molecules are said to be "substantially complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described, for example, by Sambrook, J., et al., (*In: Molecular Cloning, a Laboratory Manual, 2nd Edition, Cold Spring Harbor Press,* Cold Spring Harbor, N.Y. (1989)), and by Haymes, B. D., et al. (*In: Nucleic Acid Hybridization, A Practical Approach,* IRL Press, Washington, D.C. (1985)), both herein incorporated by reference). Departures from complete complementarity are therefore permissible, as long as such departures do not completely preclude the capacity of the molecules to form a double-stranded structure.

For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith for the purposes employed. However, for detection purposes, particularly using labeled sequence-specific probes, the primers typically have exact complementarity to obtain the best results. Thus, for an oligonucleotide to serve as an allele-specific oligonucleotide, it must generally be complementary in sequence and be able to form a stable double-stranded structure with a target polynucleotide under the particular environmental conditions employed.

The term "allele-specific oligonucleotide" refers to an oligonucleotide that is able to hybridize to a region of a target polynucleotide spanning the sequence, mutation, or polymorphism being detected and is substantially unable to hybridize to a corresponding region of a target polynucleotide that either does not contain the sequence, mutation, or polymorphism being detected or contains an altered sequence, mutation, or polymorphism. As will be appreciated by those in the art, allele-specific is not meant to denote an absolute condition. Allele-specificity will depend upon a variety of environmental conditions, including salt and formamide concentrations, hybridization and washing conditions and stringency. Depending on the sequences being analyzed, one or more allele-specific oligonucleotides may be employed for each target polynucleotide. Preferably, allele-specific oligonucleotides will be completely complementary to the target polynucleotide. However, departures from complete complementarity are permissible. In order for an oligonucleotide to serve as a primer oligonucleotide, however, it typically need only be sufficiently complementary in sequence to be able to form a stable double-stranded structure under the particular environmental conditions employed. Establishing environmental conditions typically involves selection of solvent and salt concentration, incubation temperatures, and incubation times. The terms "primer" or "primer oligonucleotide" as used herein refer to an oligonucleotide as defined herein, which is capable of acting as a point of initiation of synthesis when placed under conditions in which synthesis of a primer extension product which is complementary to a nucleic acid strand is induced, as for example, in a PCR reaction. As with non-primer oligonucleotides, primer oligonucleotides may be labeled, according to any technique known in the art, such as with radiolabels, fluorescent labels, enzymatic labels, proteins, haptens, antibodies, sequence tags, and the like.

In performing the methods of the present invention, the oligonucleotides or the target polynucleotide may be either in solution or affixed to a solid support. Generally, allele-specific oligonucleotides will be attached to a solid support, though in certain embodiments of the present invention allele-specific oligonucleotides may be in solution. In some such embodiments, the target polynucleotide is preferably bound to a solid support. In those embodiments where the allele-specific oligonucleotides or the target polynucleotides are attached to a solid support, attachment may be either covalent or non-covalent. Attachment may be mediated, for example, by antibody-antigen-type interactions, poly-L-Lys, streptavidin or avidin-biotin, salt-bridges, hydrophobic interactions, chemical linkages, LTV cross-ag, baking, and the like. In addition, allele-specific oligonucleotides can be synthesized directly on a solid support or attached to the solid support subsequent to synthesis. In a preferred embodiment, allele-specific oligonucleotides are affixed on a solid support such that a free 3'-OH is available for polymerase-mediated primer extension.

Suitable solid supports for the present invention include substrates constructed of silicon, glass, plastic (polystyrene, nylon, polypropylene, etc.), paper, etc. Solid supports may be formed, for example, into wells (as in 96-well dishes), plates, slides, sheets, membranes, fibers, chips, dishes, and beads. In certain embodiments of the present invention, the solid support is treated, coated, or derivatized so as to facilitate the immobilization of an allele-specific oligonucleotide or a target polynucleotide. Preferred treatments include coating, treating, or derivatizing with poly-L-Lys, streptavidin, antibodies, silane derivatives, low salt, or acid.

Identification of Polymorphisms

The polymorphisms of the present invention may be characterized using any of a variety of suitable methods. Suitable methods comprise direct or indirect sequencing methods, restriction site analysis, hybridization methods, nucleic acid amplification methods, gel migration methods, the use of antibodies that are specific for the proteins encoded by the different alleles of the polymorphism, or by other suitable means. Alternatively, many such methods are well known in the art and are described, for example in T. Maniatis et al, *Molecular Cloning, a Laboratory Manual, 2nd Edition,* Cold Spring Harbor Press, Cold Spring Harbor, N.Y. (1989), J. W. Zyskind et al, *Recombinant DNA Laboratory Manual,* Academic Press, Inc., New York (1988), and in R. Elles, *Molecular Diagnosis of Genetic Diseases,* Humana Press, Totowa, N.J. (1996), each herein incorporated by reference.

Identification methods may be of either a positive-type or a negative-type. Positive-type methods determine the identity of a nucleotide contained in a polymorphic site, whereas negative-type methods determine the identity of a nucleotide not present in a polymorphic site. Thus, a wild-type site may be identified either as wild-type or not mutant. For example, at a biallelic polymorphic site where the wild-type allele contains an cytosine and the mutant allele contains a adenine, a site may be positively determined to be either adenine or cytosine or negatively determined to be not adenine (and thus cytosine) or not cytosine (and thus adenine). Alternately, if the polymorphism is a deletion, or addition then the complementary sequence can be detected. As another example, in hybridization-based assay, a target polynucleotide containing a mutated site may be identified positively by hybridizing to an allele-specific oligonucleotide containing the mutated site or negatively, by failing to hybridize to a wild-type allele-specific oligonucleotide. Similarly, a restriction site may be determined to be present or lacking.

Direct Sequencing

Direct sequencing by methods such as dideoxynucleotide sequencing (Sanger), cycle sequencing, or Maxam-Gilbert sequencing are examples of suitable methods for determining the identity of a nucleotide at a polymorphic site of a target polynucleotide. Such methods are widely known in the art and are discussed at length, in the above-cited texts.

Both the dideoxy-mediated method and the Maxam-Gilbert method of DNA sequencing require the prior isolation of the DNA molecule which is to be sequenced. The sequence information is obtained by subjecting the reaction products to electrophoretic analysis (typically using polyacrylamide gels). Thus, a sample is applied to a lane of a gel, and the various species of nested fragments are separated from one another by their migration velocity through the gel. The number of nested fragments which can be separated in a single lane is approximately 200–300 regardless of whether the Sanger or the Maxam-Gilbert method is used. Thus, in order to identify a nucleotide at a particular polymorphic site in a target polynucleotide, extraneous sequence information is typically produced. The chief advantage of direct sequencing lies in its utility for locating previously unidentified polymorphic sites.

One of the problems that has encumbered the development of useful assays for genetic polymorphisms is that in many cases, it is desirable to determine the identity of multiple polymorphic loci. This frequently requires sequencing significant regions of the genome or performing multiple assays with an individual patient sample.

Restriction Site Analysis

Restriction enzymes are specific for a particular nucleotide sequence. In certain embodiments of the present invention, the identity of a nucleotide at a polymorphic site is determined by the presence or absence of a restriction enzyme site. A large number of restriction enzymes are known in the art and, taken together, they are capable of recognizing at least one allele of many polymorphisms.

This feature of restriction enzymes may be utilized in a variety of methods for identifying a polymorphic site. Restriction fragment length polymorphism (RFLP) analysis is an example of a suitable method for identifying a polymorphic site with restriction enzymes (Lentes et al., *Nucleic Acids Res.* 16:2359 (1988); and C. K. McQuitty et al., *Hum. Genet.* 93:225 (1994)). In RFLP analysis, at least one target polynucleotide is digested with at least one restriction enzyme and the resultant "restriction fragments" are separated based on mobility in a gel. Typically, smaller fragments migrate faster than larger fragments. Consequently, a target polynucleotide that contains a particular restriction enzyme recognition site will be digested into two or more smaller fragments, which will migrate faster than a larger fragment lacking the restriction enzyme site. Knowledge of the nucleotide sequence of the target polynucleotide, the nature of the polymorphic site, and knowledge of restriction enzyme recognition sequences guide the design of such assays.

Hybridization

Several suitable hybridization-based methods for identifying a nucleotide at a polymorphic site have been described. Generally, allele-specific oligonucleotides are utilized in performing such hybridization-based methods. Preferably, allele-specific oligonucleotides are chosen that are capable of specifically hybridizing to only one allele of an alpha-2A molecule at a region comprising a polymorphic site. In those embodiments wherein more than one polymorphic site is identified, sets of allele-specific oligonucleotides are preferably chosen that have melting temperatures within 5° C. of each other when hybridizing to their complete complement. Most preferably, such sets of allele-specific oligonucleotides are chosen so as to have melting temperatures within 20° C. of each other. Examples of suitable hybridization methods are described in standard manuals such as Molecular Cloning, A Laboratory Manual (2nd Ed., Sambrook, Fritsch and Maniatis, Cold Spring Harbor); and Current Protocols in Molecular Biology (Eds. Ausubel, Brent, Kingston, More, Feidman, Smith and Stuhl, Greene Publ. Assoc., Wiley-Interscience, NY, N.Y., 1992) or that are otherwise known in the art. Examples of preferred hybridization methods include Southern, northern, and dot blot hybridizations, allele-specific oligonucleotide hybridizations (Hall et al., *The Lancet* 345:1213–1214 (1995)), reverse dot blot hybridizations (Sakai et al., *Nucl. Acids. Res.* 86:6230–6234 (1989)), DNA chip hybridizations (Drmanac et al., U.S. Pat. No. 5,202,231), and hybridizations to allele-specific oligonucleotides.

Macevicz (U.S. Pat. No. 5,002,867), for example, describes a method for deriving nucleic acid sequence information via hybridization with multiple mixtures of oligonucleotide probes. In accordance with such method, the sequence of a target polynucleotide is determined by permitting the target to sequentially hybridize with sets of probes having an invariant nucleotide at one position, and a variant nucleotides at other positions. The Macevicz method determines the nucleotide sequence of the target by hybridizing the target with a set of probes, and then determining the number of sites that at least one member of the set is capable of hybridizing to the target (i.e. the number of "matches"). This procedure is repeated until each member of a sets of probes has been tested.

Polymerase-Mediated Primer Extension

The "Genetic Bit Analysis" ("GBA") method disclosed by Goelet, P. et al. (WO92/15712, and U.S. Pat. Nos. 5,888,819 and 6,004,744, all herein incorporated by reference), is a preferred method for determining the identity of a nucleotide at a predetermined polymorphic site in a target polynucleotide. The target polynucleotide can be, for example, nucleic acids encoding the alpha-2A adrenergic receptor molecule or complements or fragments thereof. GBA is a method of polymorphic site interrogation in which the nucleotide sequence information surrounding a polymorphic site in a target nucleic acid sequence is used to design an oligonucleotide primer that is complementary to a region immediately adjacent to at the 3' or 5' end of the target polynucleotide, but not including, the variable nucleotide(s) in the polymorphic site of the target polynucleotide. The target polynucleotide is isolated from the biological sample and hybridized to the interrogating primer. In some embodiments of the present invention, following isolation, the target polynucleotide may amplified by any suitable means prior to hybridization to the interrogating primer. The primer is extended by a single labeled terminator nucleotide, such as a dideoxynucleotide, using a polymerase, often in the presence of one or more chain terminating nucleoside triphosphate-precursors (or suitable, analogs). A detectable signal is thereby produced.

For example, to detect the polymorphic site on target nucleic acids encoding the alpha-2AAR, a primer oligonucleotide complementary to a region of SEQ ID NO:1 can be hybridized at the primer's 3' end to a region up to and including, for example, nucleotide position number 752 of SEQ ID NO:1. If the primer is extended at its 3' end by a single labeled terminator nucleotide, such as for example the dideoxynucleotide ddGTP, using a polymerase, a detectable signal is produced indicating the complementary nucleotide C at nucleotide position 753. This indicates the wild-type alpha-2AAR shown in FIG. 1A (bolded arrow) and thus the polymorphic alpha-2AAR is identified.

In some embodiments of the present invention, the oligonucleotide is bound to a solid support prior to the extension reaction. In other embodiments, the extension reaction is performed in solution and the extended product is subsequently bound to a solid support.

In an alternate sub-embodiment of GBA, the primer is detectably labeled and the extended terminator nucleotide is modified so as to enable the extended primer product to be bound to a solid support. An example of this would be where the primer is fluorescently labeled and the terminator nucleotide is a biotin-labeled terminator nucleotide and the solid support is coated or derivatized with avidin or streptavidin. In such embodiments, an extended primer would thus be enabled to bind to a solid support and non-extended primers would be unable to bind to the support, thereby producing a detectable signal dependent upon an a successful extension reaction.

Ligase/polymerase mediated genetic bit analysis (U.S. Pat. Nos. 5,679,524, and 5,952,174, both herein incorporated by reference) is another example of a suitable polymerase mediated primer extension method for determining the identity of a nucleotide at a polymorphic site. Ligase/polymerase GBA utilizes two primers. Generally, one primer is detectably labeled, while the other is designed to be affixed to a solid support. In alternate embodiments of ligase/polymerase GBA, extended nucleotide is detectably labeled. The primers in ligase/polymerase GBA are designed to hybridize to each side of a polymorphic site, such that there is a gap comprising the polymorphic site. Only a successful extension reaction, followed by a successful ligation reaction enables the production of the detectable signal. The method offers the advantages of producing a signal with considerably lower background than is possible by methods employing only hybridization or primer extension alone.

The present invention includes an alternate method for determining the identity of a nucleotide at a predetermined polymorphic site in a target polynucleotide. This method is described in Soderlund et al., U.S. Pat. No. 6,013,431, the entire disclosure is herein incorporated by reference. In this alternate method, the polymorphic site is interrogated where nucleotide sequence information surrounding a polymorphic site in a target nucleic acid sequence is used to design an oligonucleotide primer that is complementary to a region flanking the 3' or 5' end of the target polynucleotide, but not including, the variable nucleotide(s) in the polymorphic site of the target polynucleotide. The target polynucleotide is isolated from the biological sample and hybridized to the interrogating primer. In some embodiments of this method, following isolation, the target polynucleotide may be amplified by any suitable means prior to hybridization to the interrogating primer. The primer is extended, using a polymerase, often in the presence of a mixture of at least one labeled deoxynucleotide and one or more chain terminating nucleoside triphosphate-precursors (or suitable, analogs). A detectable signal is thereby produced upon incorporation of the labeled deoxynucleotide into the primer.

Cohen, D. et al. (PCT Application W091/02087) describes another example of a suitable method for determining the identity of a polymorphic site, wherein dideoxynucleotides are used to extend a single primer by a single nucleotide in order to determine the sequence at a desired locus. Dale et al. (PCT Application W090/09455 and U.S. Pat. No. 5,856,092) describes a method for sequencing a "variable site" using a primer in conjunction with a single dideoxynucleotide species. Ritterband, M., et al., (PCT Application W095/17676) describes an apparatus for the separation, concentration and detection of such target molecules in a liquid sample. Cheeseman, P. C. (U.S. Pat. No. 5,302,509) describes a related method of determining the sequence of a single stranded DNA molecule. The method of Cheeseman employs fluorescently labeled 3'-blocked nucleotide triphosphates with each base having a different fluorescent label.

Wallace et al. (PCT Application W089/10414) describes multiple PCR procedures which can be used to simultaneously amplify multiple regions of a target by using allele specific primers. By using allele specific primers, amplification can only occur if a particular allele is present in a sample.

Several other suitable primer-guided nucleotide incorporation procedures for assaying polymorphic sites in DNA have been described (Komher, J. S. et al., *Nucl. Acids. Res.* 17:7779–7784 (1989); Sokolov, B. P., *Nucl. Acids Res.* 18:3671 (1990); Syvdnen, A.-C., et al., *Genomics* 8:684–692 (1990); Kuppuswamy, M. N. et al., *Proc. Natl. Acad. Sci.* (*U.S.A.*) 88:1143–1147 (1991); Bajaj et al. (U.S. Pat. No. 5,846,710); Prezant, T. R. et al., *Hum. Mutat.* 1:159–164 (1992); Ugozzoli, L. et al., *GATA* 9:107–112 (1992); Nyren, P. et al., *Anal. Biochem.* 208:171–175 (1993)). These methods differ from GBA in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide will result in signals that are proportional to the length of the run (Syvdnen, A.-C., et al., *Amer. J. Hum. Genet.* 52:46–59 (1993)). Such a range of locus-specific signals could be more complex to interpret, especially for heterozygotes, compared to the simple, ternary (2:0, 1:1, or 0:2) class of signals produced by the GBA method.

Amplification

In certain embodiments of the present invention, the detection of polymorphic sites in a target polynucleotide may be facilitated through the use of nucleic acid amplification methods. Such methods may be used to specifically increase the concentration of the target polynucleotide (i.e., sequences that span the polymorphic site, or include that site and sequences located either distal or proximal to it). Such amplified molecules can be readily detected by gel electrophoresis, or other means.

The most preferred method of achieving such amplification employs PCR (e.g., Mullis, et al., U.S. Pat. No. 4,965,188), using primer pairs that are capable of hybridizing to the proximal sequences that define or flank a polymorphic site in its double-stranded form.

In some embodiments of the present invention, the amplification method is itself a method for determining the identity of a polymorphic site, as for example, in allele-specific PCR (J. Turki et al., *J. Clin. Invest.* 95:1635–1641 (1995)). In allele-specific PCR, primer pairs are chosen such that amplification is dependent upon the input template nucleic acid containing the polymorphism of interest. In such embodiments, primer pairs are chosen such that at least one primer is an allele-specific oligonucleotide primer. In some sub-embodiments of the present invention, allele-specific primers are chosen so that amplification creates a restriction site, facilitating identification of a polymorphic site. In other embodiments of the present invention, amplification of the target polynucleotide is by multiplex PCR (Wallace et al. (PCT Application W089/10414)). Through the use of multiplex PCR, a multiplicity of regions of a target polynucleotide may be amplified simultaneously. This is particularly advantageous in those embodiments wherein greater than a single polymorphism is detected.

In lieu of PCR, alternative methods, such as the "Ligase Chain Reaction" ("LCR") may be used (Barany, F., *Proc. Natl. Acad. Sci.* (*U.S.A*) 88:189–193 (1991)). LCR uses two pairs of oligonucleotide probes to exponentially amplify a specific target. The sequences of each pair of oligonucleotides is selected to permit the pair to hybridize to abutting sequences of the same strand of the target. Such hybridization forms a substrate for a template-dependent ligase. As with PCR, the resultant product serves as a template in subsequent amplification cycles, resulting in an exponential amplification of the desired sequence.

In accordance with the present invention, LCR can be performed using oligonucleotides having sequences derived from the same strand, located proximal and distal to the polymorphic site. In one embodiment, either oligonucleotide is designed so as to include the actual polymorphic site of the polymorphism. In such an embodiment, the reaction conditions are selected such that the oligonucleotides can be ligated together only if the target molecule contains the specific nucleotide in the polymorphic site that is complementary to the polymorphic site present on the oligonucleotide. In an alternative embodiment, the oligonucleotides will not include the polymorphic site, such that when they hybridize to the target molecule, a "gap" of at least one nucleotide is created (see, Segev, D., PCT Application W090/01069 and U.S. Pat. No. 6,004,826). This gap is then "filled" with complementary dNTPs (as mediated by DNA polymerase), or by an additional pair of oligonucleotides. Thus, at the end of each cycle, each single strand has a complement capable of serving as a target during the next cycle and exponential amplification of the desired sequence is obtained.

The "Oligonucleotide Ligation Assay" ("OLA") (Landegren, U. et al., *Science* 241:1077–1080 (1988)) shares certain similarities with LCR and is also a suitable method for analysis of polymorphisms. The OLA protocol uses two oligonucleotides, which are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson, D. A. et al have described a nucleic acid detection assay that combines attributes of PCR and OLA (Nickerson, D. A. et al., *Proc. Natl. Acad. Sci.* (*U.S.A.*) 87:8923–8927 (1990)). In this method, PCR is used to achieve the exponential amplification of target DNA, which is then detected using OLA.

Schemes based on ligation of two (or more) oligonucleotides in the presence of nucleic acid having the sequence of the resulting "dioligonucleotide", thereby amplifying the dioligonucleotide, are known (Wu, D. Y. et al., *Genomics* 4:560 (1989); Adams, C., W094/03630), and are also suitable methods for the purposes of the present invention.

Other known nucleic acid amplification procedures, such as transcription-based amplification systems (Malek, L. T. et al., U.S. Pat. No. 5,130,238; Davey, C. et al., European Patent Application 329,822; Schuster et al., U.S. Pat. No. 5,169,766; Miller, H. I. et al., PCT Application W089/06700; Kwoh, D. et al., *Proc. Natl. Acad. Sci.* (*U.S.A.*) 86:1173 Z1989); Gingeras, T. R. et al., PCT Application W088/10315)), or isothermal amplification methods (Walker, G. T. et al., *Proc. Natl. Acad Sci.* (*U.S.A.*) 89:392–396 (1992)) may also be used.

Gel Migration

Single strand conformational polymorphism (SSCP; M. Orita et al., *Genomics* 5:874–879 (1989); *Humphfies* et al., *In: Molecular Diagnosis of Genetic Diseases, R. Elles*, ed. pp 321–340 (1996)) and temperature gradient gel electrophoresis (TGGE; R. M. Wartell et al, *Nucl. Acids Res.* 18:2699–2706 (1990)) are examples of suitable gel migration-based methods for determining the identity of a polymorphic site. In SSCP, a single strand of DNA will adopt a conformation that is uniquely dependent of its sequence composition. This conformation is usually different, if even a single base is changed. Thus, certain embodiments of the present invention, SSCP may be utilized to identify polymorphic sites, as wherein amplified products (or restriction fragments thereof) of the target polynucleotide are denatured, then run on a non-denaturing gel. Alterations in the mobility of the resultant products is thus indicative of a base change. Suitable controls and knowledge of the "normal" migration patterns of the wild-type alleles may be used to identify polymorphic variants.

TGGE is a related procedure, except that the nucleic acid sample is run on a denaturing gel. In embodiments of the present invention utilizing TGGE to identify a polymorphic site, the amplified products (typically PCR products) are electrophoresed over denaturing polyacrylamide gel, wherein the temperature gradient is optimized for separation of the target polynucleotide segments (E. Reihsaus et al., *Am. J. Respir. Cell Mol. Biol.* 8:334–339 (1993), herein incorporated by reference). This method is able to detect single base changes in the target polynucleotide sequence.

In the most preferred embodiment, the present invention includes methods of genotyping nucleic acids encoding an alpha-2A adrenergic receptor molecule from a sample of an individual which includes isolating from the individual the sample having a polynucleotide encoding the alpha-2A adrenergic receptor molecule identified as SEQ ID NO: 1 or 2 or fragment or complement thereof; incubating the polynucleotide with at least one oligonucleotide, the oligonucleotide having a nucleotide sequence that is complementary to a region of the polynucleotide, and which, when hybridized to the region permits the identification of the nucleotide present at a polymorphic site of the polynucleotide, wherein the incubation is under conditions sufficient to allow specific hybridization to occur between complementary nucleic acid molecules; permitting the hybridization to occur; and identifying the polymorphic site to obtain the genotype of the individual. A genotype includes an unphased 5' to 3' sequence of nucleotide pair(s) found at one or more polymorphic sites in a locus on a pair of homologous chromosomes in an individual.

As used herein, the term "genotyping" refers to determining the presence, absence or identity of a polymorphic site in a target nucleic acid (identified as SEQ ID NOs: 1 or 2).

In one embodiment, genotyping involves obtaining a sample containing the target nucleic acid, treating the sample to obtain single stranded nucleic acids, if such nucleic acid is double-stranded, so as to obtain unpaired nucleotide bases spanning the specific position. If the target nucleic acid is single-stranded, this step is not necessary. The sample containing the target nucleic acid is contacted with a oligonucleotide under hybridizing conditions. The oligonucleotide is capable of hybridizing with a stretch of nucleotide bases present in the target nucleic acid, adjacent to the polymorphic site to be identified (e.g., deletion, mutation, or a single nucleotide polymorphisms), so as to form a duplex between the oligonucleotide and the target nucleic acid. When the oligonucleotide is "immediately adjacent" the polymorphic site to be identified, the oligonucleotide hybridizes with the target nucleic acid in such a way that either the 3' or 5' end of the oligonucleotide is complementary to a nucleotide on the target nucleic acid that is located immediately 5' or 3', respectively, of the polymorphic site to be identified. It is also contemplated herein that the oligonucleotide can be a fragment complementary to SEQ ID NO: 1 or 2, and not immediately adjacent to the polymorphic site to be identified, such that the 3' end of the oligonucleotide is 1 up to 50, preferably 1 up to 10, nucleotides upstream or downstream from the polymorphic site to be identified in the target nucleic acid.

As used herein, upstream includes that part of a strand of DNA or RNA molecule that is towards the 5'end of the polymorphic site or site of interest. For example, upstream of the polymorphic site (nucleotide position 753 of SEQ ID NO: 1 or 2) includes nucleotide positions 752 to 732. Downstream includes that part of a strand of DNA or RNA molecule lying towards the 3' end of the polymorphic site or site of interest. For example, downstream of the polymorphic site (nucleotide position 753 of SEQ ID NO: 1 or 2) includes nucleotide positions nucleotide positions 754 to 764.

In one embodiment of the present invention, to detect the polymorphic site on target nucleic acids encoding the alpha-2AAR, a primer oligonucleotide complementary to a region of SEQ ID NO:1 can be hybridized at the primer's 3' end to a region up to and including, for example, nucleotide position number 752 of SEQ ID NO:1. If the primer is extended at its 3' end by a single labeled terminator nucleotide, such as for example the dideoxynucleotide ddGTP, using a polymerase, a detectable signal is produced indicating the complementary nucleotide C at nucleotide position 753. This indicates the wild-type alpha-2AAR shown in FIG. 1A (bolded arrow) and thus the polymorphic alpha-2AAR is identified.

The above described genotyping methods are useful in determining the frequency of the alpha-2AAR genotype or haplotype in a population. The method comprises determining the genotype or the haplotype pair for the alpha-2AAR gene that is present in each member of the population and calculating the frequency any particular alpha-2AAR genotype or haplotype is found in the population. Haplotyping includes a method for determining the haplotype of an individual. As used herein, a haplotype includes a phased 5' to 3' sequence of nucleotides found at two or more polymorphic sites in a locus on a single chromosome from a single individual.

In a preferred embodiment, the alpha-2AAR genotype may also comprise the nucleotide pair(s) detected at one or more additional alpha-2AAR polymorphic sites. The population may be a reference population, a family population, a same sex population, a population group, a trait population (e.g., a group of individuals exhibiting a trait of interest such as a medical condition or response to a therapeutic treatment). Population groups include a group of individuals sharing a common ethno-geographic origin. Reference populations include a group of subjects or individuals who are predicted to be representative of the genetic variation found in the general population. Preferably, the reference population represents the genetic variation in the population at a certainty level of at least 85%, preferably at least 90%, more preferably at least 95% and even more preferably at least 99%.

Frequency data for such alpha-2AAR genotypes or haplotypes in reference and trait populations are useful for identifying an association between a trait and an alpha-2AAR polymorphism, an alpha-2AAR genotype or an alpha-2AAR haplotype. The trait may be any detectable phenotype, including but not limited to genetic predisposition to a disease or response to a treatment. The method comprises obtaining data on the frequency of the alpha-2AAR polymorphism, alpha-2AAR genotype or alpha-2AAR haplotype of interest in a reference population as well as in a population exhibiting the trait. Frequency data for one or both of the reference and trait populations may be obtained by genotyping or haplotyping each individual in the populations using one of the methods described herein. In another embodiment, the frequency data for the reference and/or trait populations is obtained by accessing previously determined frequency data, which may be in written or electronic form. For example, the frequency data may be present in a database that is accessible by a computer. Once the frequency data is obtained, the frequencies of the alpha-2AAR polymorphism, alpha-2AAR or alpha-2AAR haplotype of interest are compared in the reference and trait populations. If a alpha-2AAR polymorphism, alpha-2AAR genotype or alpha-2AAR haplotype is more frequent in the trait population than in the reference population to a statistically significant degree, then the trait is predicted to be associated with that alpha-2AAR polymorphism, alpha-2AAR genotype or alpha-2AAR haplotype.

In a preferred embodiment of the method, the trait of interest is a clinical response exhibited by a patient to some therapeutic treatment, for example, response to a drug targeting alpha-2AAR or response to a therapeutic treatment for a medical condition. As used herein, "medical condition" includes but is not limited to any condition or disease manifested as one or more physical and/or psychological symptoms for which treatment is desirable, and includes previously and newly identified diseases and other disorders. As used herein the term "clinical response" means any or all of the following: a quantitative measure of the response, no response, and adverse response (i.e., side effects).

In order to deduce a correlation between a clinical response to a treatment and an alpha-2AAR, alpha-2AAR genotype or alpha-2AAR haplotype, the clinician can obtain data on the clinical responses exhibited by a population of individuals who received the treatment, hereinafter the "clinical population". This clinical data may be obtained by analyzing the results of a clinical trial that has already been run and/or the clinical data may be obtained by designing and carrying out one or more new clinical trials. As used herein, the term "clinical trial" means any research study designed to collect clinical data on responses to a particular treatment, and includes but is not limited to phase I, phase II and phase III clinical trials. Standard methods are used to define the patient population and to enroll subjects.

It is preferred that the individuals included in the clinical population have been assessed for the clinical characteristics of the medical condition of interest. Such clinical characteristics may include symptoms, disease severity, response to therapy and the like. Characterization of potential patients could employ a standard physical exam or one or more lab tests.

The therapeutic treatment of interest is administered to each individual in the trial population and each individual's response to the treatment is measured using one or more predetermined criteria. It is contemplated that in many cases, the trial population will exhibit a range of responses and that the investigator will choose the number of responder groups (e.g., none, low, medium, high) made up by the various responses. In addition, the alpha-2AAR gene for each individual in the trial population is genotyped at least one polymorphic site occurring in the alpha-2AAR, which may be done before or after administering the treatment. As used herein, treatment includes a stimulus (i.e., drug) administered internally or externally to an individual.

After both the clinical and polymorphism data have been obtained, correlations are created between individual response and the presence of the alpha-2AAR polymorphism, alpha-2AAR genotype or alpha-2AAR haplotype. Correlations may be produced in several ways. In one embodiment, individuals are grouped by their alpha-2AAR genotype or alpha-2AAR haplotype and then the averages and standard deviations of clinical responses exhibited by the member of each group are calculated. These results are then analyzed to determine if any observed variation in clinical response between genotype or haplotype groups is statistically significant. Another method involves categorizing the response (e.g., none, low, medium, high or other such grades) and then assessing whether a particular genotype is more common in one group of responders compared to another. Statistical analysis methods which may be used are described in L. D. Fisher and G. vanbelle, "Biostatistics: A Methodology for the Health Sciences", Wiley-Interscience (New York) 1993.

It is also contemplated that the above methods for identifying associations between an alpha-2AAR polymorphism, or alpha-2AAR genotypes and haplotypes containing the alpha-2AAR polymorphism, may be performed in combination with genotype(s) and haplotype(s) for one or more additional genomic regions.

Kits of the Present Invention

The present invention provides diagnostic and therapeutic kits that include at least one primer for detecting at least one polymorphism in nucleic acids encoding an alpha-2A adrenergic receptor molecule. Preferably, the kit includes a container having an oligonucleotide comprising a region of SEQ ID NOs: 1 or 2 or complement thereof for detecting the polymorphism as described. In one embodiment, the kit includes primers for amplifying regions of nucleic acids encoding the alpha-2A adrenergic receptor molecule where at least one of the polymorphisms is found, such as for example SEQ ID NOs: 1 or 2. In an alternate embodiment, the kit includes allele-specific oligonucleotides, specific for both mutant and wild-type alleles of at least one polymorphism. The kit may also contain sources of "control" target polynucleotides, as positive and negative controls. Such sources may be in the form of patient nucleic acid samples, cloned target polynucleotides, plasmids or bacterial strains carrying positive and negative control DNA. Kits according to the invention can include one or more containers, as well as additional reagent(s) and/or active and/or inert ingredient(s) for performing any variations on the methods of the invention. Exemplary reagents include, without limitation, one or more primers, one or more terminator nucleotides, such as dideoxynucleotides, that are labeled with a detectable marker. The kits can also include instructions for mixing or combining ingredients or use.

Providing Nucleic Acids Encoding Alpha-2A Adrenergic Receptor

The alpha-2A-adrenergic receptor molecule identified as SEQ ID NO: 3 or 4 or fragments thereof and DNA encoding the protein (alpha-2A-adrenergic receptor molecule) may also be chemically synthesized by methods known in the art. Suitable methods for synthesizing the protein are described by Stuart and Young in "Solid Phase Peptide Synthesis," Second Edition, Pierce Chemical Company (1984), Solid Phase Peptide Synthesis, Methods Enzymol., 289, Academic Press, Inc, New York (1997). Suitable methods for synthesizing DNA are described by Caruthers in Science 230: 281–285 (1985) and DNA Structure, Part A: Synthesis and Physical Analysis of DNA, Lilley, D. M. J. and Dahlberg, J. E. (Eds.), Methods Enzymol., 211, Academic Press, Inc., New York (1992).

The nucleic acid sequences of the present invention that encode or express the polymorphic alpha-2A-adrenergic receptor molecule identified as SEQ ID NO: 3 or 4 or fragments thereof, can be formed from a variety of different polynucleotides (i.e., genomic DNA or cDNA, RNA, synthetic oligonucleotides, etc.). In the most preferred embodiment, the polynucleotides encode the alpha-2A-adrenergic receptor molecule. Such polynucleotides comprise SEQ ID NO: 1 or 2 or fragment thereof or complement thereof.

Accordingly, the nucleic acid molecules or cDNA encoding the alpha-2A adrenergic receptor molecule identified as SEQ ID NO: 1 or 2 or fragment or complement thereof can be synthesized chemically from the four nucleotides in whole or in part by methods known in the art. Such methods include those described by Caruthers in Science 230:281–285 (1985) and DNA Structure, Part A: Synthesis and Physical Analysis of DNA, Lilley, D. M. J. and Dahlberg, J. E. (Eds.), Methods Enzymol., 211, Academic Press, Inc., New York (1992).

DNA may also be synthesized by preparing overlapping double-stranded oligonucleotides, filling in the gaps, and ligating the ends together. The DNA may be cloned in a suitable recombinant host cell and expressed. The DNA and protein may be recovered from the host cell. See, generally, Sambrook, J. et al. (Eds.), Molecular Cloning, Second Edition, Cold Spring Harbor Laboratory Press, Cold Spring Harbor, N.Y. (1989) and Ausubel, F. M. et al. (Eds.), Current Protocols in Molecular Biology, John Wiley & Sons, Inc., New York (1999).

The nucleic acid molecules or DNA encoding the alpha-2A adrenergic receptor molecule identified as SEQ ID NO: 1 or 2 of the invention may be replicated and used to express recombinant protein following insertion into a wide variety of host cells in a wide variety of cloning and expression vectors. The host may be prokaryotic or eukaryotic. The DNA may be obtained from natural sources and, optionally, modified. The genes may also be synthesized in whole or in part.

Cloning vectors may comprise segments of chromosomal, non-chromosomal and synthetic DNA sequences. Some suitable prokaryotic cloning vectors include plasmids from *E. coli*, such as colE1, pCR1, pBR322, pMB9, pUC, pKSM, and RP4. Prokaryotic vectors also include derivatives of phage DNA such as M13 and other filamentous single-stranded DNA phages.

Vectors for expressing proteins in bacteria, especially *E. coli*, are also known. Such vectors include the pK233 (or any of the tac family of plasmids), T7, pBluescript II, bacteriophage lamba ZAP, and lambda $P_L$ (Wu, R. (Ed.), Recombinant DNA Methodology II, Methods Enzymol., Academic Press, Inc., New York, (1995)). Examples of vectors that express fusion proteins are PATH vectors described by Dieckmann and Tzagoloff in J. Biol. Chem. 260, 1513–1520 (1985). These vectors contain DNA sequences that encode anthranilate synthetase (TrpE) followed by a polylinker at the carboxy terminus. Other expression vector systems are based on beta-galactosidase (pEX); maltose binding protein (pMAL); glutathione S-transferase (pGST or PGEX)—see Smith, D. B. Methods Mol. Cell Biol. 4:220–229 (1993); Smith, D. B. and Johnson, K. S., Gene 67:31–40 (1988); and Peptide Res. 3:167 (1990), and TRX (thioredoxin) fusion protein (TRXFUS)—see LaVallie, R. et al., Bio/Technology 11:187–193 (1993). A particularly preferred plasmid of the present invention is pBC12BI.

Vectors useful for cloning and expression in yeast are available. Suitable examples are 2 μm circle plasmid, Ycp50, Yep24, Yrp7, Yip5, and pYAC3 (Ausubel, F. M. et al. (Eds.), Current Protocols in Molecular Biology, John Wiley & Sons, Inc., New York, (1999)).

Suitable cloning/expression vectors for use in mammalian cells are also known. Such vectors include well-known derivatives of SV-40, adenovirus, cytomegalovirus (CMV) retrovirus-derived DNA sequences. Any such vectors, when coupled with vectors derived from a combination of plasmids and phage DNA, i.e. shuttle vectors, allow for the isolation and identification of protein coding sequences in prokaryotes.

Further eukaryotic expression vectors are known in the art (e.g., P. J. Southern and P. Berg, J. Mol. Appl. Genet. 1:327–341 (1982); S. Subramani et al, Mol. Cell. Biol. 1:854–864 (1981); R. J. Kaufmann and P. A. Sharp, "Amplification And Expression Of Sequences Cotransfected with A Modular Dihydrofolate Reductase Complementary DNA Gene," J. Mol. Biol. 159:601–621 (1982); R. J. Kaufmann and P. A. Sharp, Mol. Cell. Biol. 159:601–664 (1982); S. I. Scahill et al, "Expression And Characterization Of The Product Of A Human Immune Interferon DNA Gene In Chinese Hamster Ovary Cells," Proc. Natl. Acad. Sci. USA 80:4654–4659 (1983); G. Urlaub and L. A. Chasin, Proc. Natl. Acad. Sci. USA 77:4216–4220 (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, the let system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Useful expression hosts include well-known prokaryotic and eukaryotic cells. Some suitable prokaryotic hosts include, for example, *E. coli*, such as *E. coli* SG-936, *E. coli* HB 101, *E. coli* W3110, *E. coli* X1776, *E. coli* X2282, *E. coli* DH1, *E coli* DH5alphaF, and *E. coli* MRC1, *Pseudomonas, Bacillus*, such as *Bacillus subtilis*, and *Streptomyces*. Suitable eukaryotic cells include yeasts and other fungi, insect, animal cells, such as COS cells and CHO cells, human cells and plant cells in tissue culture. A particularly preferred host cell is CHO.

Transgenic Animals

The knowledge of the alpha-2A-adrenergic receptor molecule identified as amino acids SEQ ID NO: 3 or 4 of the invention, together with the cloning and sequencing of the nucleic acids encoding the alpha-2A-adrenergic receptor molecule identified as SEQ ID NO: 1 or 2, enables other applications of the invention. For example, genetically altered animals can be constructed using techniques, such as transgenesis and gene ablation with substitution, to express alpha-2A-adrenergic receptor gene products. Various such techniques are known, and certain of these techniques can yield heritability of the transgene. See, e.g., Pinkert et al. (1995) for an overview of these techniques, and the documents cited there for greater detail. Also, the production of transgenic non-human animals is disclosed U.S. Pat. Nos. 5,175,385, 5,175,384, 5,175,838 and 4,736,866 which are incorporated herein by reference.

Briefly, an animal can be transformed by integration of an expressible transgene comprising a heterologous alpha-2A-adrenergic receptor-related nucleic acid sequence into the genome of the animal. Preferably the transgene is heritable. Such a transgenic animal can then be used as an in vivo model for production of the alpha-2A-adrenergic receptor molecule in the species from which the gene encoding the alpha-2A-adrenergic receptor molecule is derived. Of particular importance, of course, is the development of animal models for human alpha-2A-adrenergic receptor activity. Such transgenic animal models would express, for example, the mutant alpha-2A-adrenergic receptor molecule normally expressed in humans, and would be capable of being used as in vivo pharmacologic models to study polymorphisms and effects on receptor activity. In gene ablation with substitution (also called "hit and run" or "tag and replace") the murine alpha-2A gene is removed and replaced with the human wild-type or mutant alpha-2A gene.

Animals suited for transgenic manipulation include domesticated animals, simians and humans. Domesticated animals include those of the following species: canine; feline; bovine; equine; porcine; and murine.

In one exemplary approach a genetically altered test animal is administered a putative alpha-2A-adrenergic receptor agonist or antagonist. Following a time sufficient to produce a measurable effect in an otherwise untreated animal, binding and activity of the agonist or antagonist is measured by methods known in the art, such as radio-ligand binding assays, adenyl cyclase, MAP kinase or inositol phosphate activity. A lower than normal rate of binding or activity indicates that the receptor is defective.

Providing Alpha-2A Adrenergic Receptor Molecules

The alpha-2A adrenergic receptor molecule identified as SEQ ID NO: 3 or 4 can be the entire protein as it exists in nature, or an antigenic, preferably immunogenic, fragment of the whole protein. Antigenic and/or immunogenic fragments of antigenic and/or immunogenic proteins may be identified by methods known in the art.

Fragments containing antigenic sequences may be selected on the basis of generally accepted criteria of potential antigenicity and/or exposure. Such criteria include the hydrophilicity and relative antigenic index, as determined by surface exposure analysis of proteins. The determination of appropriate criteria is known to those skilled in the art, and has been described, for example, by Hopp, T., Methods Enzymol., 178:571–585 Academic Press, Inc., New York (1989); Becker, Y., Virus Genes 6:79–93 (1992); Regenmortel, V and Pellequer, J. L., Pept. Res. 7:224–228 (1994); Gallet, X. et al., Prot. Eng. 8:829–834 (1995); Kyte et al., J. Mol. Biol. 157:105–132 (1982); Emini, E. A. et al., J. Virol. 55:836–839 (1985); Jameson et al., CA BIOS 4:181–186 (1988); and Karplus et al., Naturwissenschaften 72:212–213 (1985). Amino acid domains predicted by these criteria to be surface exposed are selected preferentially over domains predicted to be more hydrophobic or hidden.

Methods for isolating and identifying antigenic fragments from known antigenic proteins are described by Salfeld et al. in J. Virol. 63:798–808 (1989) and by Isola et al. in J. Virol. 63:2325–2334 (1989). An alternative means for identifying antigenic sites on protein is by the use of synthetic peptide combinatorial library or phage-display peptide library as described in Combinatorial Peptide Library Protocols, Cabilly, S. (Ed.), Humana Press, New York, 1998; Pinilla, C. et al., Pept. Res. 8:250–257 (1995); Scala, G. et al., J. Immunol. 162:6155–6161 (1999); Pereboeva, L. A. et al., J. Med. Virol. 56:105–111 (1998); and Demkowicz, W. E. et al., J. Virol. 66:386–398 (1992).

As previously stated, the alpha-2A adrenergic receptor molecule and fragments of the present invention may be prepared by methods known in the art. Such methods include isolating the protein directly from cells, isolating or synthesizing DNA encoding the protein and using the DNA to produce recombinant protein, and synthesizing the protein chemically from individual amino acids.

Isolation of Alpha-2A-Adrenergic Receptor Molecule from Solution and Gels

The alpha-2A adrenergic receptor molecule is isolated from the solubilized fraction of the protein by standard methods. Some suitable methods include precipitation and liquid/chromatographic protocols such as ion exchange, hydrophobic interaction and gel filtration See, for example, Guide to Protein Purification, Deutscher, M. P. (Ed.) Methods Enzymol., 182, Academic Press, Inc., New York (1990) and Scopes, R. K. and Cantor, C. R. (Eds.), Protein Purification (3d), Springer-Verlag, New York (1994).

Alternatively, purified material is obtained by separating the protein on preparative SDS-PAGE gels, slicing out the band of interest and electroeluting the protein from the polyacrylamide matrix by methods known in the art. The detergent SDS is removed from the protein by known methods, such as by dialysis or the use of a suitable column, such as the Extracti-Gel column from Pierce.

Antibodies

The present invention provides antibodies raised against the alpha-2A-adrenergic receptor protein identified as SEQ ID NO: 3 or 4 or fragment thereof. Such antibodies can bind, preferably specifically, with amino acid position 251 of SEQ ID NO: 3 or 4. These antibodies form the basis of a diagnostic test or kits. An "antibody" in accordance with the present specification is defined broadly as a protein that binds specifically to an epitope, such as for example the lysine at amino acid position 251 of SEQ ID NO: 4 or fragment thereof. The antibody may be polyclonal or monoclonal. Antibodies further include recombinant polyclonal or monoclonal Fab fragments prepared in accordance with the method of Huse et al., Science 246, 1275–1281 (1989) and Coligan, J. E. et al. (Eds.) Current Protocols in Immunology, Wiley Intersciences, New York, (1999).

Preparing Antibodies

Polyclonal antibodies are isolated from mammals that have been innoculated with the protein or a functional analog, such as in accordance with methods known in the art (Coligan, J. E, et al. (Eds.), Current Protocols in Immunology, Wiley Intersciences, New York, (1999)). Briefly, polyclonal antibodies may be produced by injecting a host mammal, such as a rabbit, mouse, rat, or goat, with the protein or a fragment thereof capable of producing antibodies that distinguish between mutant and wild-type protein. The peptide or peptide fragment injected may contain the wild-type sequence or the mutant sequence. Sera from the mammal are extracted and screened to obtain polyclonal antibodies that are specific to the peptide or peptide fragment.

The antibodies are preferably monoclonal. Monoclonal antibodies may be produced by methods known in the art. These methods include the immunological method described by Kohler and Milstein in Nature 256:495–497 (1975) and by Campbell in "Monoclonal Antibody Technology, The Production and Characterization of Rodent and Human Hybridomas" in Burdon et al. (Eds.), Laboratory Techniques in Biochemistry and Molecular Biology, Volume 13, Elsevier Science Publishers, Amsterdam (1985); and Coligan, J. E, et al. (Eds.), Current Protocols in Immunology, Wiley Intersciences, New York, (1999); as well as the recombinant DNA method described by Huse et al., Science 246:1275–1281 (1989).

In order to produce monoclonal antibodies, a host mammal is inoculated with a peptide or peptide fragment as described above, and then boosted. Spleens are collected from inoculated mammals a few days after the final boost. Cell suspensions from the spleens are fused with a tumor cell in accordance with the general method described by Kohler and Milstein in Nature 256:495–497 (1975). See also Campbell, "Monoclonal Antibody Technology, The Production and Characterization of Rodent and Human. Hybridomas" in Burdon et al. (Eds.), Laboratory Techniques in Biochemistry and Molecular Biology, Volume 13, Elsevier Science Publishers, Amsterdam (1985) and Coligan, J. E., et al. (Eds.), Current Protocols in Immunology, Wiley Intersciences, New York, (1999)). In order to be useful, a peptide fragment must contain sufficient amino acid residues to define the epitope of the molecule being detected.

If the fragment is too short to be immunogenic, it may be conjugated to a carrier molecule. Some suitable carrier molecules include keyhold limpet hemocyanin and bovine serum albumin. Conjugation may be carried out by methods known in the art (Coligan, J. E. et al. (Eds.) Current Protocols in Immunology, Chapter 9, Wiley Intersciences, New York, (1999)). One such method is to combine a cysteine residue of the fragment with a cysteine residue on the carrier molecule.

Methods for preparing polyclonal and monoclonal antibodies that exhibit specificity toward single amino acid differences between peptides are described by McCormick et al. in U.S. Pat. No. 4,798,787. These methods are incorporated herein by reference.

Predicting Individual's Response and Selecting Appropriate Drugs

The polymorphisms and molecules of the present invention can be used to predict an individual's sensitivity or responsiveness to a pharmaceutical composition or drug, such as for example, an agonists or antagonists. Preferably, the individual's response to an agonist or antagonist, includes detecting a polymorphism in the nucleic acids encoding the alpha-2A adrenergic receptor molecule comprising SEQ ID NOs:1 or 2 or fragment or complement thereof, and correlating the polymorphism to a predetermined response thereby predicting the individual's response to the agonist or antagonist. Accordingly, the present invention can be employed to guide the clinician in the selection of appropriate drug(s) or pharmaceutical composition(s). For example, individuals with a polymorphism comprising lysine at amino acid position 251 of (SEQ ID NO. 4) in the alpha-2AAR molecule are less sensitive to antagonists since endogenous agonist activation of the receptor by catecholamines is increased. Accordingly, with regards to agonists, the response or sensitivity can be predicted to be greater for those individuals with the polymorphism comprising lysine at amino acid position 251 of the alpha-2AAR due to impaired coupling.

Figure 3A:
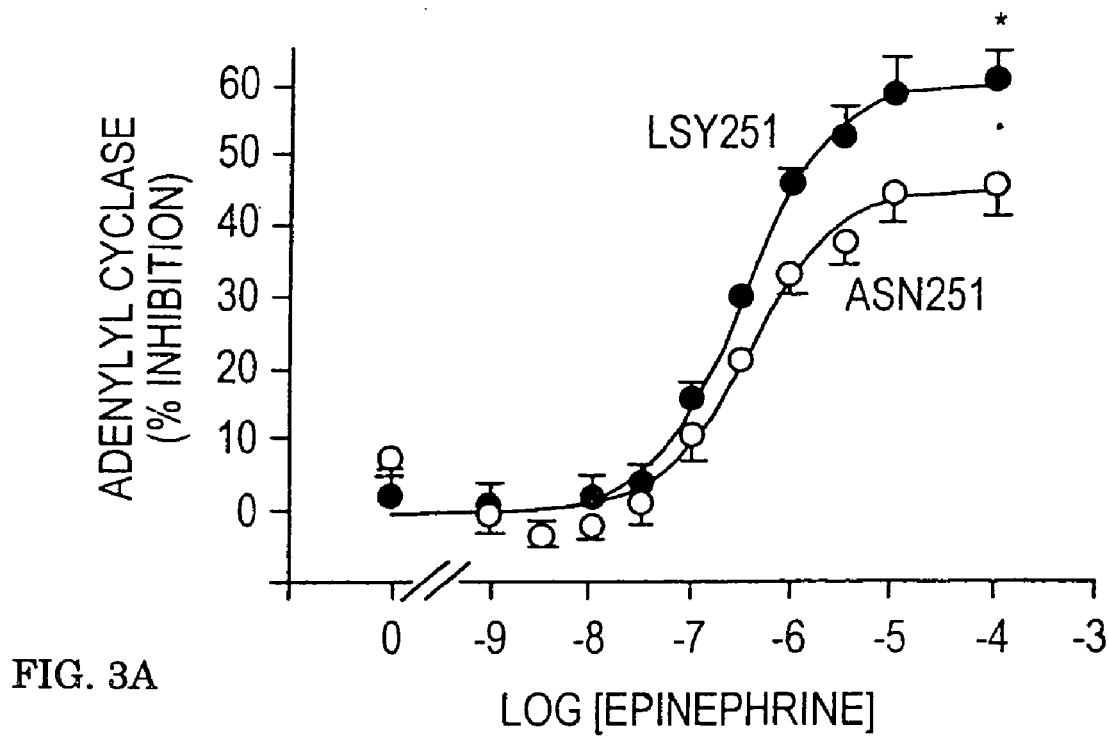
FIG. 3 is a graphic illustration of the coupling of the wild-type Asn251 and polymorphic Lys251 alpha-2AARs to the inhibition of adenylyl cyclase. Membranes from CHO cells were prepared and adenylyl cyclase activities determined as described below in the presence of 5.0 µM forskolin and the indicated concentrations of the full agonist epinephrine (Graph A) and the partial agonist oxymetazoline (Graph B). Results as shown are the percent inhibition of forskolin stimulated activities from clones at matched levels of expression (~2500 fmol/mg) from 5 individual experiments each (*indicates p<0.05 for the maximal inhibition compared to wild-type for both agonists).
Figure 3B:
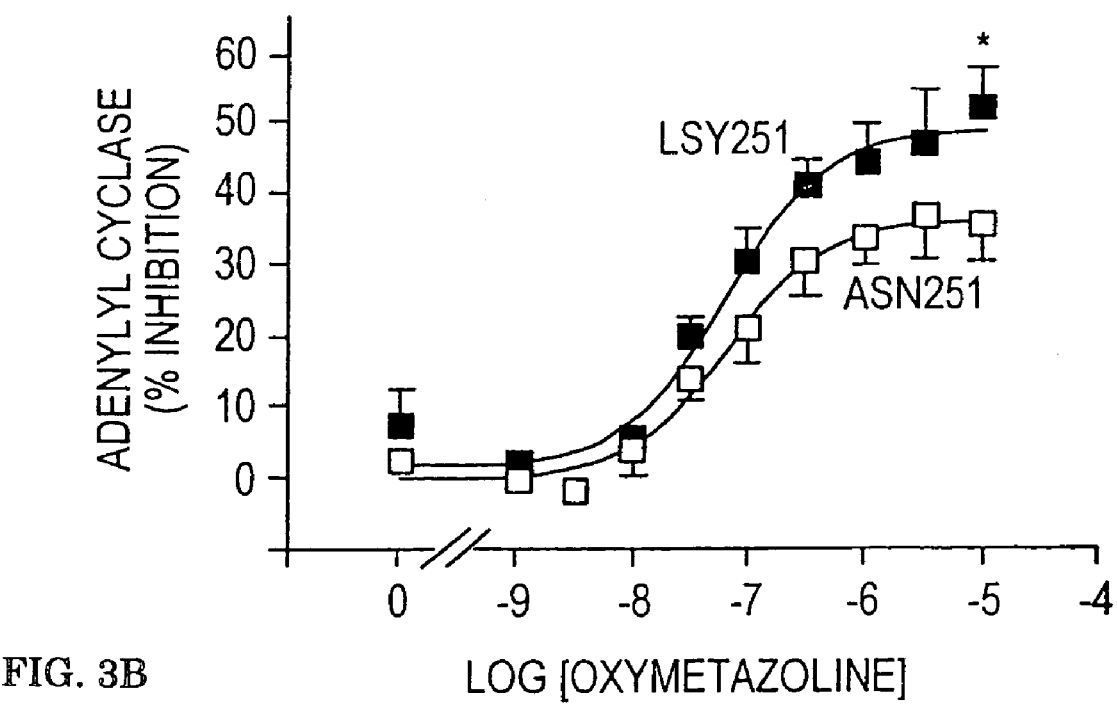

Alpha-2A adrenergic receptor molecule function or activity can be measured by methods known in the art. Some examples of such measurement include radio-ligand binding to the alpha-2A adrenergic receptor molecule by an agonist or antagonist, receptor-G protein binding, stimulation or inhibition of adenyl cyclase, MAP kinase or inositol phosphate (IP3). In one embodiment of the present invention, an alpha-2A adrenergic receptor agonist is administered, the agonist activates the alpha-2AAR molecule and $G_i$ coupling results in inhibiting adenylyl cyclase, stimulation of MAP kinase, or stimulation of IP3. In this embodiment of the present invention, the polymorphic or mutant alpha-2AAR shows increased inhibition of adenylyl cyclase (FIG. 3A-B), increased stimulation of MAP kinase (FIG. 5B) and increased receptor-G protein binding (GTPγ5 binding, FIG. 4) as compared to the wild-type alpha-2AAR with asparagine at amino acid position 251 SEQ ID NO: 3. Thus, the polymorphic alpha-2AAR has enhanced receptor activity or function. In another embodiment of the present invention, the polymorphic alpha-2AAR shows increased MAP kinase as compared to the wild-type alpha-2AAR. Thus, mutant or polymorphic alpha-2AAR has enhanced receptor activity or function. Preferably, receptor activity is measured by increased or decreased adenyly cyclase, MAP kinase, G protein receptor interaction and/or inositol phosphate. Increased or decreased adenyly cyclase, MAP kinase and/or inositol phosphate includes increases or decreases of preferably from about 10% to about 200%, more preferably, from about 20% to about 100%, and most preferably, from about 30% to about 60% over normal levels.

For purposes of the present invention, an agonist is any molecule that activates a receptor. Preferably, the receptor is an alpha-2AAR. Preferred agonist include alpha-2A adrenergic receptor agonists, such as for example, epinephrine, norepinephrine, clonidine, oxymetazoline, guanabenz, UK14304, BHT933 and combinations thereof.

An antagonist is any molecule that blocks a receptor. Preferably, the receptor is an alpha-2AAR. Preferred antagonist include alpha-2A adrenergic receptor antagonists such as for example, yohimbine, prazosin, ARC 239, rauwolscine, idazoxan, tolazoline, phentolamine and combinations thereof.

As used herein a "predetermined response" includes a measurable or baseline effect of the agonist or antagonist correlated with the polymorphism. For example, individuals with the polymorphism wild-type Asn 251 of the alpha-2A adrenergic receptor molecule display depressed alpha agonist promoted coupling to $G_i$ and thus decreased inhibition of adenylyl cyclase compared to the polymorphic or mutant alpha-2AAR. Other baseline secondary messenger molecules can be used and correlated to the polymorphism, such as MAP kinase and inositol phosphate (See FIGS. 5 and 6).

The present invention includes methods for selecting an appropriate drug or pharmaceutical composition to administer to an individual having a disease associated with alpha-2A adrenergic receptor molecule. The method includes detecting a polymorphism in nucleic acids encoding the alpha-2A adrenergic receptor molecule comprising SEQ ID NOs: 1 or 2 or fragment or complement thereof in the individual and selecting the appropriate drug based on the polymorphsim present. The appropriate drug or pharmaceutical composition can be determined by those skilled in the art based on the particular polymorphism identified. For example, individuals with a polymorphism comprising lysine at amino acid position 251 of (SEQ ID NO. 4) in the alpha-2AAR molecule are less sensitive to antagonists since endogenous agonist activation of the receptor by endogenous catecholamines is increased. Accordingly, with regards to agonists, the response or sensitivity can be predicted to be greater for those individuals with the polymorphism comprising lysine at amino acid position 251 of the alpha-2AAR due to impaired coupling. This would lead the clinician to select an agonist or alternative drug(s) is indicated.

As used herein, "appropriate pharmaceutical composition" includes at least one drug that increases therapeutic efficacy of the drug based on a patient population with a particular disease. Each population will typically have a unique characteristic response to the drug. Knowledge of the efficacies of two or more drugs in treating individuals with different genetic variations provides the opportunity to select the drug effective in treating a large percentage of the total population of individuals while maintaining little or no toxicity.

For example, the lysine 251 polymorphism which results in a gain in alpha-2AAR function occur at a lower rate in Caucasians. In contrast, the allelic frequency, thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions used in the present methods may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drugs, it is desirable to slow the absorption from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredients in finely divided form may be used in admixture with a larger-sized pharmaceutically acceptable inert carrier comprising particles having a size, for example, of up to 100 μm in diameter. Suitable inert carriers include sugars such as lactose. Desirably, at least 95% by weight of the particles of the active ingredient have an effective particle size in the range of 0.01 to 10 μm.

Alternatively, the composition or drugs may be pressurized and contain a compressed gas, such as nitrogen or a liquefied gas propellant. The liquefied propellant medium and indeed the total composition is preferably such that the active ingredients do not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye. The active compounds are delivered in a pharmaceutically acceptable ophthalmic vehicle, such that the compounds are maintained in contact with the ocular surface for a sufficient time period to allow the compounds to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the active compounds with suitable non-irritating excipients or carriers such as cocoa butter, polyethylene glycol or a suppository wax which are solid at room temperature but liquid at body temperature and therefore melt in the rectum or vaginal cavity and release the drugs.

The compositions used in the methods of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form, in addition to one or more of the active compounds described above, can contain stabilizers, preservatives, excipients and the like. The preferred lipids are the phospholipids and the phosphatidyl cholines (lecithins), both natural and synthetic.

Typical dosages and durations of treatment are as described in clinician's textbooks such as Physician's Desk Reference 2000, incorporated herein by reference, and will be familiar to physicians and other practitioners in the art.

Figure 4:
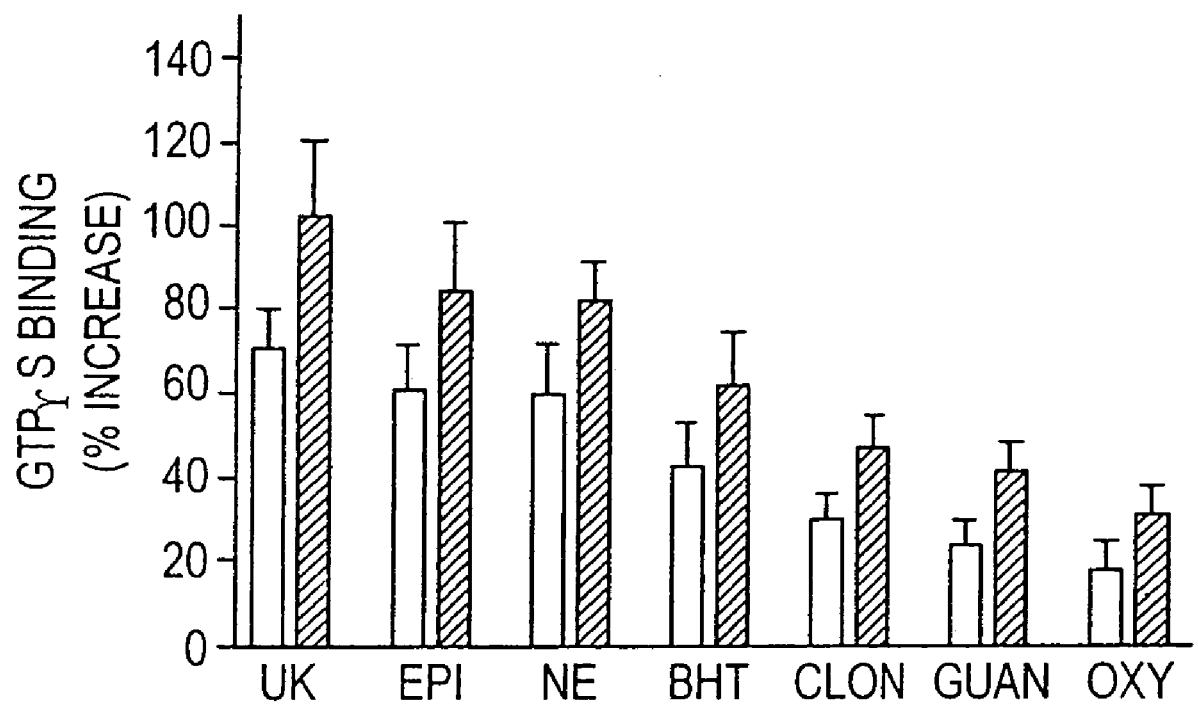
FIG. 4 is a bar graph illustration of wild-type Asn251 and polymorphic Lys251 alpha-2AAR promoted [$^{35}$S]GTPγS binding in response to full and partial agonists. Binding of [$^{35}$S]GTPγS was measured in membranes from COS-7 cells transiently coexpressing the wild-type and Lys251 alpha-2AAR and $G_{i\alpha2}$ as described below. Assays were carried out using 10 µM of the agonists UK 14304, epinephrine, norepinephrine, BHT-933, clonidine, guanabenz, and oxymetazoline. Results are shown as % increase over basal levels from three or more experiments.
Figure 5:
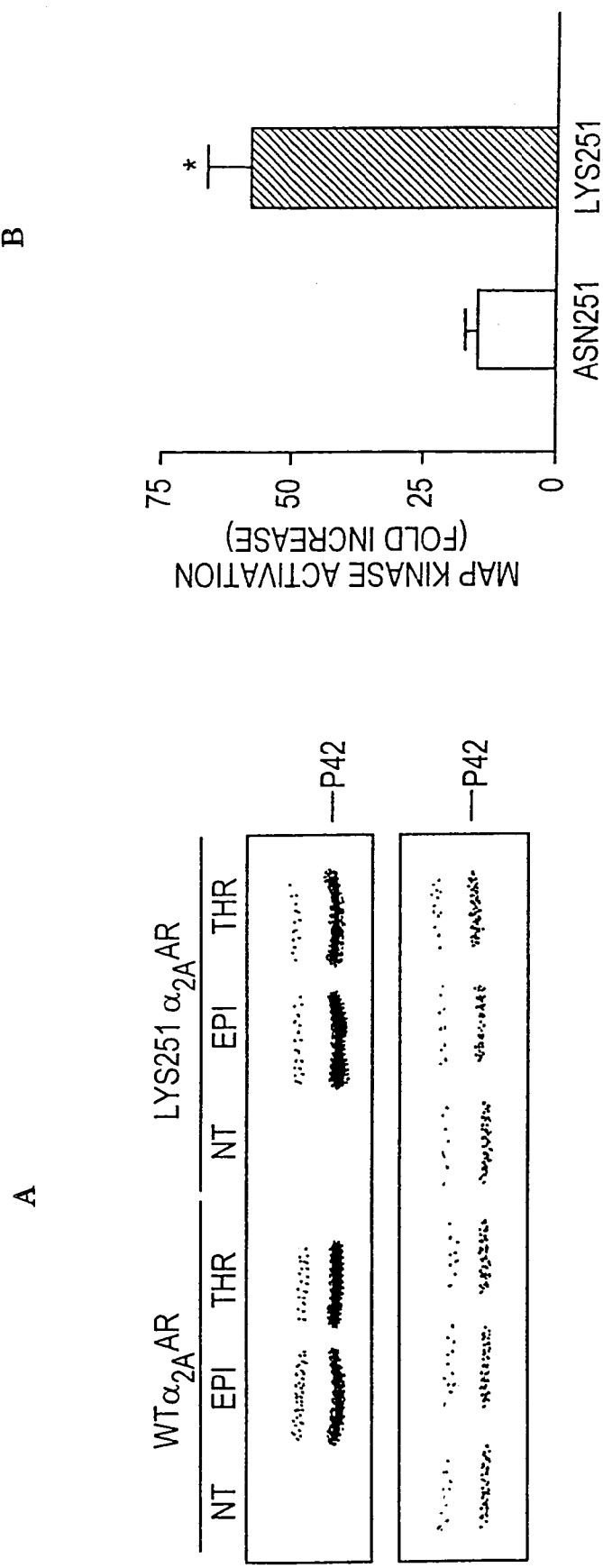
FIG. 5 illustrates stimulation of MAP kinase by wild-type and Lys251 alpha-2AARs. Phosphorylation of MAP kinase was determined in CHO cells by quantitative immunoblotting with enhanced chemifluorescence using antibodies specific for phosphorylated Erk 1/2. The same blots were stripped and reprobed for total MAP kinase expression, which was not significantly different between the two cell lines (Panel A). Cells were studied after incubation with carrier (basal), 10 µM epinephrine, or 1 unit/ml thrombin. Results are shown as the fold-stimulation over basal levels (Panel B). The * indicates p<0.05 compared to the wild-type response (n=3 experiments).

In one preferred embodiment of the present invention, after detecting a polymorphism, such as for example, Asn 251 or Lys 251 of alpha-2AAR molecule, the percent adenylyl cyclase inhibition, GTPγS binding, MAP kinase stimulation or IP3 production is used to determine receptor function. For example, FIG. 4 illustrates drugs that have increased GTPγS binding and thus increased alpha-2AAR activity. Of the drugs tested, the alpha-2AAR agonists epinephrine and UK 14304 have the highest percentage increase in GTPγS binding in individual's with lysine at amino acid position 251 of the alpha-2AAR molecule. Therefore, these drugs would be considered appropriate agonists to use for treatment of disease in patients that have Lys 251 polymorphism of the alpha-2AAR molecule, provided such patients are in need of agonist treatment.

In this regard, pharmacodynamic data can be developed and correlated with drug receptor interaction and function to establish a predetermined response in individuals. As used herein, "correlating the polymorphism with a predetermine response" includes associating the predetermined response with the polymorphism that occurs at a higher allelic frequency or rate in individuals with the polymorphism than without. Correlation of the polymorphism with the response can be accomplished by bio-statistical methods known in the art, such as for example, Chi-squared tests or other methods described in L. D. Fisher and G. vanBelle, *Biostatistics: A Methodology for the Health Sciences*, Wiley-Interscience (New York) 1993.

The above methods of the present invention can be used in vivo, in vitro, and ex vivo, for example, in living mammals as well as in cultured tissue, organ or cellular systems. Mammals include, for example, humans, as well as pet animals such as dogs and cats, laboratory animals, such as rats and mice, hamsters and farm animals, such as horses and cows. Tissues, as used herein, are an aggregation of similarly specialized cells which together perform certain special functions. Cultured cellular systems include any cells that express the alpha-2AAR molecule, such as pre and post synaptic neurons in the brain or any cell transfected with the alpha-2A gene.

Having now generally described the invention, the same may be more readily understood through the following reference to the following examples, which are provided by way of illustration and are not intended to be limit the present invention unless specified.

EXAMPLES

The examples below describe a single nucleotide polymorphism occuring in nucleic acids encoding the alpha-2AAR molecule. This polymorphism results in an Asn to Lys substitution at amino acid 251 of the third intracellular loop of the alpha-2AAR molecule. The frequency of Lys251 was 10-fold greater in African-Americans compared to Caucasians, but was not associated with essential hypertension. To determine the consequences of this substitution, wild-type and Lys251 receptors were expressed in CHO and COS-7 cells. Expression, ligand binding, and basal receptor function were unaffected by the substitution. However, agonist-promoted [$^{35}$S]GTPγS binding was ~40% greater with the Lys251 receptor. In studies of agonist-promoted functional coupling to $G_i$, the polymorphic receptor displayed enhanced inhibition of adenylyl cyclase (60±4.4 vs 46±4.1% inhibition) and markedly enhanced stimulation of MAP kinase (57±9 vs 15±2 fold increase over basal) compared to wild-type alpha-2AAR. This enhanced agonist function was observed with catecholamines, azepines and imadazolines. In contrast, agonist stimulation of phospholipase C was not different between the two receptors. Unlike previously described variants of G protein coupled receptors where the minor species causes either a loss of function or increased non-agonist function, Lys251 alpha-2AAR can represent another class of polymorphism whose phenotype is a gain of agonist-promoted function.

Example 1

Polymorphism Detection

The intronless wild-type human alpha-2AAR gene identified as SEQ ID NO: 1 (GenBank Accession #AF281308 which includes the sequenic corrections illuminated by Guyer et al, 1990) was amplified by overlapping PCR reactions from genomic DNA derived from blood samples. The 1350 bp coding sequence as well as 341 bp 5'UTR and 174 bp 3'UTR were examined. For convenience, the adenine of the initiator ATG codon is designated as nucleotide 1 and amino acid 1 is the encoded methionine. The human receptor consists of 450 amino acids. For initial examination, DNA from 27 hypertensive individuals was utilized. Overlapping PCR products encompassing the $\alpha_{2A}$ gene were designated fragments 1–5 and were generated using the following primers: Fragment 1 (600 bp), 5'-TTTACCCATCG-GCTCTCCCTAC-3' (sense) SEQ ID NO: 5 and 5'-GAGA-CACCAGGAAGAGGTTTTGG-3' (antisense) SEQ ID NO: 6; Fragment 2 (467 bp) 5'-TCGTCATCATCGCCGTGTTC-3' (sense) SEQ ID NO: 7 and 5'-CGTACCACTTCTG-GTCGTTGATC-3' (antisense) SEQ ID NO: 8; Fragment 3 (556 bp), 5'-GCCATCATCATCACCGTGTGGGTC-3' (sense) SEQ ID NO: 9 and 5'-GGCTCGCTCGGGCCT-TGCCTTTG-3'(antisense) SEQ ID NO: 10; Fragment 4 (436 bp), 5'-GACCTGGGAG GAGAGCTCGTCTT-3' (sense) SEQ ID NO: 11 and 5'-TGACCGGGTTCAAC-GAGCTGTTG-3' (antisense) SEQ ID NO: 12; and Fragment 5 (353 bp), 5'-GCCACGCACGCTCTTCAAATTCT-3'(sense) SEQ ID NO: 13 and 5'-TTCCCTTGTAGGAGCAGCAGAC-3' (antisense) SEQ ID NO: 14. The 5' end of each sense and antisense primer also contained sequence corresponding to the M13 Forward (5'-TGTAAAACGACGGCCAGT) SEQ ID NO: 15 and M13 Reverse (5'-CAGGAAACAGCTATGACC) SEQ ID NO: 16 universal sequencing primers, respectively. The PCR consisted of ~100 ng genomic DNA, 5 pmol of each M13 primer, 0.8 mM dNTPs, 10% DMSO, 2.5 units Platinum taq DNA polymerase (Gibco/BRL), 20 uL 5× buffer A (Invitrogen) in a 100 µl reaction volume. Reactions were started by an initial incubation at 94° C. for four minutes, followed by 35 cycles of 94° C. for 30 seconds, denaturation for 30 seconds, and 72° C. for one minute, followed by a final extension at 72° C. for seven minutes. The denaturation temperature was 56° C. for fragments 1 and 5, 58° C. for fragments 2 and 4, and 60° C. for fragment 3. PCR reactions were purified using QIAQUICK™ PCR purification system (Qiagen), and automated sequencing of both strands of each PCR product was performed using an Applied Biosystems sequencer using dye primer methods. As discussed, a C to G transversion at nucleotide 753 was identified that resulted in an asparagine to lysine change at amino acid 251 (shown in FIG. 1). This nucleotide change results in gain of a unique Sty I restriction endonuclease site in PCR fragment 3, and the presence or absence of this polymorphism in additional samples wasstudied by Sty I digestion of fragment 3 PCR products (shown in FIG. 1, Panel D). This rapid detection technique was applied to additional DNA samples providing genotypes at this locus from a total of 376 individuals (normotensive: 125 Caucasian and 99 African-American; hypertensive: 75 and 77 respectively). Normotensive and hypertensive patients were selected as described previously by (Rutkowski, M. P., Klanke, C. A., Su, Y. R., Reif, M., and Menon, A. G. (1998) *Hypertension* 31, 1230–1234).

Example 2

Constructs and Cell Transfection

To create the polymorphic alpha-2AAR Lys251 construct, a portion of the coding region of alpha-2AAR gene containing a G at nucleotide position 753 was amplified from a homozygous individual using fragment 2 sense and fragment 4 antisense primers (see PCR conditions described in Example 1). This fragment was digested with and subcloned into the Bgl II and Sac II sites of the wild type $\alpha_{2A}AR$ sequence in the expression vector pBC12B1. Chinese hamster ovary cells (CHO-K1) were permanently transfected by a calcium phosphate precipitation technique as previously described using 30 µg of each receptor construct and 3.0 µg of $pSV_2neo$ to provide for G418 resistance by the methods of Eason, M. G. and Liggett, S. B. (1992) *J. Biol. Chem.* 267, 25473–25479). Selection of positive clones was carried out in 1.0 mg/ml G418 and expression of the alpha-2AAR from individual clonal lines was determined by radioligand binding as described below. Cells were grown in monolayers in Ham's F-12 medium supplemented with 10% fetal calf serum, 100 units/ml penicillin, 100 µg/ml streptomycin and 80 µg/ml G418 (to maintain selection pressure) at 37° C. in a 5% $CO_2$ atmosphere. COS-7 cells were co-transfected with 1–10 µg of each alpha-2AAR construct and ~5 µg $G_{i\alpha}$ using a DEAE-dextran method essentially as described previously by Jewell-Motz, E. A. and Liggett, S. B. (1996) *J. Biol. Chem.* 271, 18082–18087). These transfections also included 5 µg of the large T antigen containing plasmid, pRSVT (de chasseval, R. and de Villartay, J.-P. (1991) *Nucleic Acids Research* 20, 245–250), to maximize expression of the $\alpha_{2A}AR$ gene from the SV40 promoter of pBC12B1.

Example 3

Adenylyl Cyclase Activities

Alpha-2AAR inhibition of adenylyl cyclase was determined in membrane preparations from CHO cells stably expressing the two receptors using methods similar to those previously described (Eason, M. G., Moreira, S. P., and Liggett, S. B. (1995) *J. Biol. Chem.* 270, 4681–4688). Reactions consisted of 20 µg cell membranes, 2.7 mM phosphoenolpyruvate, 50 µM GTP, 0.1 mM cAMP, 0.12 mM ATP, 50 µg/ml myokinase, 0.05 mM ascorbic acid and 2 µCi of $[\alpha^{-32}P]ATP$ in a buffer containing 40 mM HEPES, pH 7.4, 1.6 mM $MgCl_2$ and 0.8 mM EDTA for 30 minutes at 37° C. Reactions were terminated by the addition of a stop solution containing excess ATP and cAMP and ~100,000 dpm of [³H]cAMP. Labeled cAMP was isolated by gravity chromatography over alumina columns with [³H]cAMP used to quantitate column recovery. Activities were measured in the presence of water (basal), 5 µM forskolin, and 5 µM forskolin with the indicated concentrations of agonists. Results are expressed as percent inhibition of forskolin stimulated activity.

Example 4

[³⁵S]GTPγS Binding

Receptor-G protein interaction was quantitated by [³⁵S] radiolabeled guanosine-5'-O-(3-thiotriphosphate) ([³⁵S] GTPγS) binding in COS-7 cells transiently transfected with each alpha-2AAR construct and $G_{i\alpha2}$. Briefly, cell membranes (~20 µg) were incubated in buffer containing 25 mM Tris-HCl, pH 7.4, 5 mM $MgCl_2$, 1 mM EDTA, 1 mM dithiotheritol, 100 mM NaCl, 1 µM GDP, and 2 nM [³⁵S] GTPγS in a 100 µl reaction volume for 15 min at room temperature. Incubations were terminated by dilution with 4 volumes of ice cold 10 mM Tris-HCL, pH 7.4 buffer and vacuum filtration over Whatmann GF/C glass fiber filters. Nonspecific binding was measured in the presence of 10 µM GTPγS.

Example 5

MAP kinase Activation

Activation of p44/42 MAP kinase was determined by quantitative immunoblotting using specific antibodies to identify phosphorylated and total MAP kinase expression. Briefly, confluent cells were incubated overnight in serum-free media prior to treatment with media alone (basal), epinephrine (10 µM), or thrombin (1 unit/ml) for 5 min. Cells were washed three times with phosphate-buffered saline (PBS) then lysed in RIPA buffer (20 mM Tris, pH 7.5, 150 mM NaCl, 1 mM EDTA, 1% NP-40, 0.5% deoxycholate, 0.1% SDS, and 5 mM NaF) containing protease inhibitors (10 µg/ml benzamidine, 10 µg/ml soybean trypsin inhibitor, 10 µg/ml aprotinin, and 5 µg/ml leupeptin). Western blots of these whole cell lysates were performed essentially as previously described (Jewell-Motz, E. A., Donnelly, E. T., Eason, M. G., and Liggett, S. B. (1998) *Biochem* 37, 15720–15725). Membranes were incubated with phospho-p44/42 MAP kinase E10 antibody (New England Biolabs, Beverly, Mass.) at a dilution of 1:2000 for 1 hr at room temperature. Washed membranes were subsequently incubated with anti-mouse fluorescein-linked immunoglobulin followed by incubation with fluorescein alkaline phosphatase (ECF, Amersham). Fluorescent signals were quantitated by real-time acquisition using a Molecular Dynamics STORM imager. After stripping, membranes were incubated under the same conditions as described in Example 4 with a p44/42 MAP kinase monoclonal antibody to quantitate total MAP kinase expression.

Example 6

Inositol Phosphate Accumulation

Total inositol phosphate levels in intact cells were determined essentially as described previously (Schwinn, D. A., Page, S. O., Middleton, J. P., Lorenz, W., Liggett, S. B., Yamamoto, K., Caron, M. G., Lefkowitz, R. J., and Cotecchia, S. (1991) *Mol. Pharmacol.* 40, 619–626). Briefly, confluent CHO cells stably expressing each of the alpha-2ARRs were incubated with [³H]myoinositol (5 µCi/ml) in media lacking fetal calf serum for 16 hrs at 37° C. in 5% $CO_2$ atmosphere. Subsequently, cells were washed and incubated with PBS for 30 min followed by a 30 min incubation with 20 mM LiCl in PBS. Cells were then treated with PBS alone (basal), varying concentrations of epinephrine, or 5 units/ml thrombin for 5 min, and inositol phosphates were extracted as described by Martin (Martin, T. F. J. (1983) *J Biol Chem* 258, 14816–14822). Following separation on Agl-X8 columns, total inositol phosphates were eluted with a solution containing 0.1 M formic acid and 1 M formate.

Example 7

Radioligand Binding

Expression of mutant and wild-type alpha-2AAR was determined using saturation binding assays as described (Eason, M. G., Jacinto, M. T., Theiss, C. T., and Liggett, S. B. (1994) *Proc. Natl. Acad. Sci., USA* 91, 11178–11182) with 12 concentrations (0.5–30 nM) of [$^3$H]yohimbine and 10 μM phentolamine used to define nonspecific binding. For competition studies, membranes were incubated in 50 mM Tris-HCL, pH 7.4, 10 mM MgSO$_4$, 0.5 mM EDTA with 2.0 nM [$^3$H]yohimbine and 16 concentrations of the indicated competitor in the presence of 100 μM GppNHp for 30 minutes at 37° C. Reactions for the above radioligand binding studies were terminated by dilution with 4 volumes of ice cold 10 mM Tris-HCL, pH 7.4 buffer and vacuum filtration over Whatmann GF/C glass fiber filters.

Example 8

Protein Determination and Data Correlation

Protein determinations were by the copper bicinchoninic acid method (Smith, P. K., Krohn, R. I., Hermanson, G. T., Mallia, A. K., Gartner, F. H., Provenzano, M. D., Fujimoto, E. K., Goeke, N. M., Olson, B. J., and Klenk, D. C. (1985) *Anal. Biochem.* 150, 76–85). Data from adenylyl cyclase and radioligand binding assays were analyzed by iterative least-square techniques using Prizm software (GraphPad, San Diego, Calif.). Agreement between genotypes observed and those predicted by the Hardy-Weinberg equilibrium was assessed by a Chi-squared test with one degree of freedom. Genotype comparisons were by Fisher's exact test. Comparisons of results from biochemical studies were paired by t-tests and significance was considered when p<0.05. Data are provided as means±standard errors.

Results and Discussion of Examples 1–8

Sequence analysis of the entire coding region of the alpha-2AAR gene from 54 chromosomes revealed one non-synonymous sequence variant located within the third intracellular loop of the receptor (FIG. 1). This consisted of a C to G transversion at nucleotide 753 that changed amino acid 251 from Asn to Lys (FIG. 2). While the Lys251 receptor is relatively rare, it is ~10 fold more common in African-Americans than in Caucasians, with an allele frequency of 0.05 as compared to 0.004 (p=0.01). The distribution of homozygous and heterozygous alleles was not different than that predicted from Hardy-Weinberg equilibrium (p>0.9). Two previously unreported synonymous single nucleotide polymorphisms were also identified at nucleic acids 849 (C to G) and 1093 (C to A). Considering the role of the alpha-2AAR in regulating blood pressure, we also determined the frequency of this polymorphism in patients with essential hypertension. Our analysis of 99 normotensive and 77 hypertensive African-Americans as well as 125 normotensive and 75 hypertensive Caucasians showed no differences in the frequency of this polymorphism in patients with essential hypertension in either group.

The consequences of this polymorphism on ligand binding and receptor function were evaluated by permanently expressing the human wild-type alpha-2AAR and the Lys251 polymorphic receptor in CHO cells. Saturation radioligand binding studies revealed essentially identical dissociation binding constants for the alpha-2AAR antagonist [$^3$H]yohimbine ($K_d$=3.4±0.21 vs 3.6±0.25 nM respectively, n=4), and competition binding assays showed no differences in binding of the agonist (−) epinephrine ($K_i$=593±65 vs 734±31 nM respectively, n=3, Table 2). These data show that the ligand binding pocket composed of the transmembrane spanning domains is not perturbed by the presence of Lys at amino acid 251 in the third intracellular loop. The Lys251 polymorphism occurs in a highly conserved portion of the third intracellular loop of the $\alpha_{2A}$AR (FIG. 2), in a region thought to be important for G-protein interaction (Eason, M. G. and Liggett, S. B. (1996) *J. Biol. Chem.* 271, 12826–12832). Indeed, as shown in FIG. 2, Asn is present in the position analogous to human 251 in all mammalian alpha-2AARs reported to date.

To assess whether this polymorphism affects G-protein coupling, functional studies examining agonist-promoted inhibition of forskolin-stimulated adenylyl cyclase activities were carried out in cell lines expressing the wild type Asn251 receptor and the polymorphic Lys251 receptor at levels of 2360±263 and 2590±140 fmol/mg (n=5, p>0.05), respectively.

TABLE 1

Pharmacological Properties of the Asn251 and Lys251 $\alpha_{2A}$ARs expressed in CHO cells.

| | Radioligand Binding | | | Adenylyl cyclase activity | |
|---|---|---|---|---|---|
| Receptor | $\beta_{max}$ (fmol/mg) | $^3$H-Yohimbine $K_D$ (nM) | Epinephrine $K_1$ (nM) | Basal (pmol/min/mg) | Forskolin (pmol/min/mg) |
| Asn251 | 2360 ± 263 | 3.4 ± 0.21 | 593 ± 65 | 11.9 ± 2.3 | 32.7 ± 4.0 |
| Lys251 | 2590 ± 140 | 3.6 ± 0.25 | 734 ± 31 | 13.9 ± 1.6 | 31.6 ± 6.5 |

As shown in Table 1, basal and 5.0 μM forskolin-stimulated adenylyl cyclase activities were not different between Asn251 and Lys251 expressing cell lines, indicating that non-agonist dependent function is equivalent with the two receptors. However, activation of the polymorphic Lys251 receptor with the full agonist epinephrine resulted in enhanced inhibition of adenylyl cyclase activity compared to wild-type alpha-2AARs. Maximal inhibition of adenylyl cyclase was 60±4.4% with the variant receptor compared to 46±4.1% with wild-type (n=5, p<0.005, FIG. 3a). Similar results were also found when receptors were activated by the partial agonist oxymetazoline, with the Lys251 having an 40% augmented function compared to the Asn251 receptor (50±6.6% vs 35±4.7% inhibition, n=5, p<0.05, FIG. 3b). No significant differences in the EC$_{50}$ values for epinephrine (583±196 nM vs 462±145 nM) or for oxymetazoline (54.0±7.3 nM vs 67.3±15.7 nM) were observed.

This enhanced function was also found by quantitating agonist-promoted receptor-G$_i$ interaction with [$^{35}$S]GTPγS binding. In these experiments, Asn251 and Lys251 receptors were transiently coexpressed in COS-7 cells (2.3±0.3 vs 2.2±1.4 pmol/mg) along with G$_{i\alpha2}$, and binding of [$^{35}$S]GTPγS was measured in membranes exposed to vehicle (basal) or saturating concentrations of various agonists.

Here, full and partial agonists with diverse structures were utilized. As is shown in FIG. 4, the Lys251 receptor had increased [$^{35}$S]GTPγS binding in response to all agonists tested, albeit to varying degrees. Basal [$^{35}$S]GTPγS binding was equivalent. Stimulation with the full agonists UK 14304, epinephrine, and norepinephrine resulted in ~40% enhanced GTPγS binding for the Lys251 receptor as compared to the Asn251 receptor. On the other hand, partial agonists displayed from 45% (BHT-933) up to 72% (guanabenz) enhancement of [$^{35}$S]GTPγS binding with the Lys251 receptor. These results are consistent with the adenylyl cyclase activity studies which also showed enhanced function of the polymorphic receptor. In addition, they indicate that the gain-of-function phenotype is more pronounced with some, but not all, partial agonists compared to full agonists.

We next investigated agonist-mediated modulation of MAP kinase by wild-type and the Lys251 receptor. Alpha-2AAR act to stimulate MAP kinase activity and thus can potentially regulate cell growth and differentiation (Luttrell, L. M., van Biesen, T., Hawes, B. E., Della Rocca, G. J., Luttrell, D. K., and Lefkowitz, R. J. (1998) in *Catecholamines: Bridging Basic Science with Clinical Medicine* (Goldstein, D. S., Eisenhofer, G., and McCarty, R., eds) pp. 466–470, Academic Press). While noting that regulation of MAP kinase activity is both receptor and cell-type specific, MAP kinase activation by alpha-2A receptors appears to be initiated by βγ released from $G_i$ (Luttrell, L. M., van Biesen, T., Hawes, B. E., Della Rocca, G. J., Luttrell, D. K., and Lefkowitz, R. J. (1998) in *Catecholamines: Bridging Basic Science with Clinical Medicine* (Goldstein, D. S., Eisenhofer, G., and McCarty, R., eds) pp. 466–470, Academic Press).

To investigate the extent of MAP kinase activation in CHO cell lines expressing both the Asn251 and Lys251 receptors, quantitative immunoblots using an antibody specific to the activated (phosphorylated) form of ERK 1/2 were performed. While the total amount of MAP kinase was not different (FIG. 5A), agonist-promoted stimulation of MAP kinase activity was markedly different between the two cell lines (FIG. 5A, B). Activation of the Lys251 receptor with 10 μM epinephrine resulted in a 57±9 fold increase in MAP kinase activity over basal as compared to 15±2.1 fold increase with the Asn251 receptor (n=3, p=<0.05).

Figure 6:
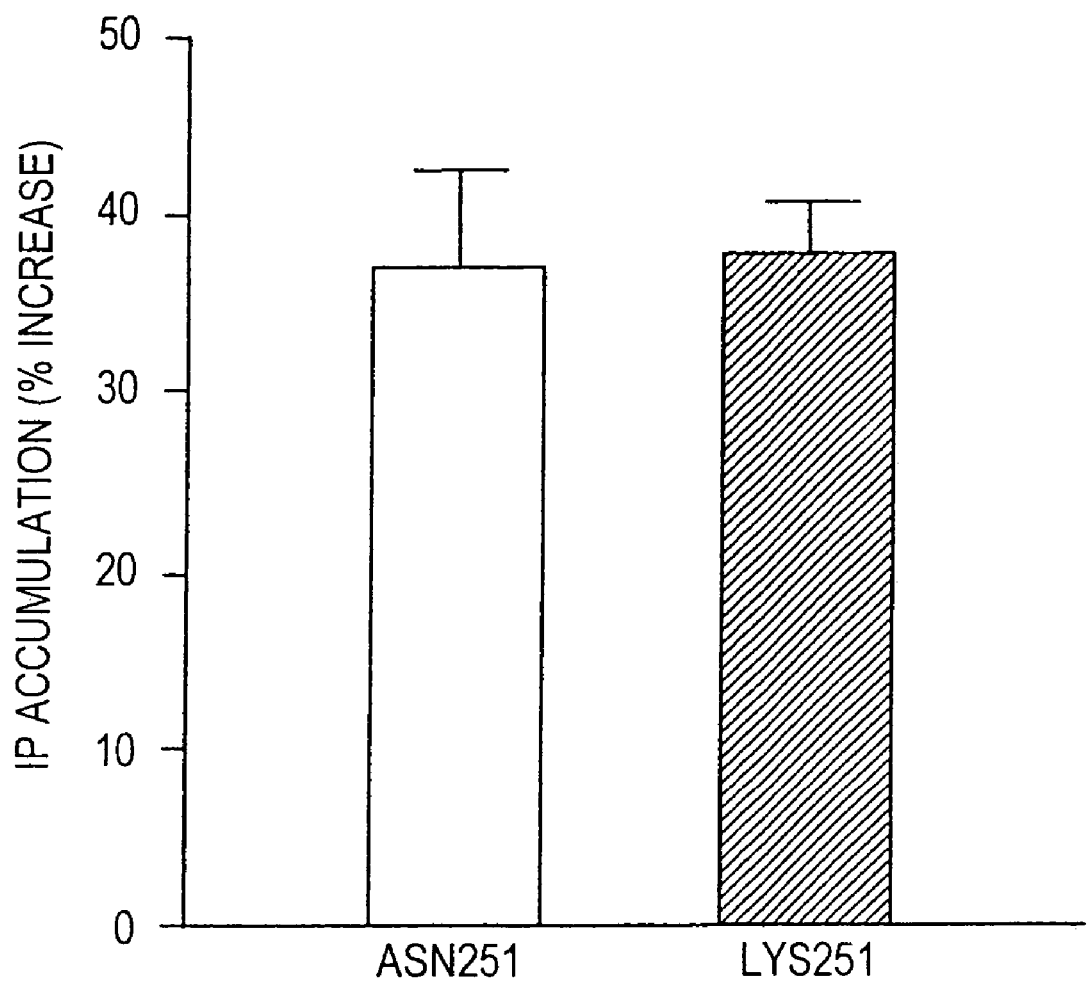
FIG. 6 is a bar graph illustration of stimulation of inositol phosphate accumulation by wild-type Asn251 and polymorphic Lys251 alpha-2AARs. Total inositol phosphate production in intact CHO cells was measured as described below in response to a 5 minute exposure to 10 µM epinephrine. Results are from five experiments.

Finally, coupling of these two receptors to the stimulation of inositol phosphate production was examined. Such $α_2$AR signaling is a complex response due to activation of phospholipase C by βγ released from activated $G_o$ and $G_i$ (Exton, J. H. (1996) *Annu Rev Pharmacol Toxicol* 36, 481–509). In contrast to the [$^{35}$S]GTPγS binding, adenylyl cyclase, and MAP kinase results, the maximal extent of epinephrine-stimulated accumulation of inositol phosphates was not found to be different between Lys251 and Asn251 expressing cells (FIG. 6). However, the signal transduction of the LYS251 receptor was nevertheless enhanced, as evidenced by a decrease in the $EC_{50}$ (wildtype=493 mm, Lys251=119 mm, P<0.05).

Alpha-2AARs are widely expressed throughout the nervous system and peripheral tissues. Recent work with relatively selective agonists and antagonists, radiolabels, and specific molecular probes in several species, including genetically engineered mice, have begun to elucidate specific functions for the various alpha-2AAR subtypes (MacMillan, L. B., Lakhlani, P., Lovinger, D., and Limbird, L. E. (1998) *Recent Prog Horm Res* 53, 25–42). The latter studies have been particularly useful in identifying subtype-specific functions. Mice lacking alpha-2AARs have higher resting systolic blood pressures and more rapidly develop hypertension with sodium loading after subtotal nephrectomy than wild-type mice (Makaritsis, K. P., Johns, C., Gavras, I., Altman, J. D., Handy, D. E., Bresnahan, M. R., and Gavras, H. (1999) *Hypertension* 34, 403–407). Furthermore, these alpha-2AAR knock-out mice fail to display a hypotensive response to the agonist dexmedetomidine (Altman, J. D., Trendelenburg, A. U., MacMillan, L., Bernstein, D., Limbird, L., Starke, K., Kobilka, B. K., and Hein, L. (1999) *Mol. Pharmacol.* 56, 154–161). Heart rates in these mice were increased at rest, which correlated with increased [$^3$H] norepinephrine release from cardiac sympathetic nerves. These data thus indicate that the presynaptic inhibition of neurotransmitter release in cortical and cardiac nerves serves important homeostatic functions in blood pressure and cardiac function. And, that the physiologic effects of therapeutic agonists such as clonidine reduce blood pressure by specifically acting at the alpha-2AAR subtype. The lack of a hypotensive effect of alpha-2AAR agonists has also been shown in genetically altered (hit-and-run) mice expressing a dysfunctional alpha-2AAR (D79N) (MacMillan, L. B., Hein, L., Smith, M. S., Piascik, M. T., and Limbird, L. E. (1996) *Science* 273, 801–805). These mice also responded poorly to alpha-2AAR agonists for several other physiologic functions (Lakhlani, P. P., MacMillan, L. B., Guo, T. Z., McCool, B. A., Lovinger, D. M., Maze, M., and Limbird, L. E. (1997) *Proc Natl Acad Sci USA* 94,9950–9955). Dexmedetomidine failed to reduce rotarod latency or induce prolongation of sleep time, to enhance the efficacy of halothone, or to attenuate thermally induced pain in these mice. Thus the sedative, anesthetic-sparing, and analgesic effects of alpha-2AAR agonists are due to activation of the alpha-2AAR subtype. Indeed, these physiologic defects correlated with absent $α_{2A}$AR regulation of inwardly rectifying K$^+$ channels of locus ceruleus neurons and voltage gated Ca$^{2+}$ channels of these same neurons, as well as those of the superior cervical ganglion (Lakhlani, P. P., MacMillan, L. B., Guo, T. Z., McCool, B. A., Lovinger, D. M., Maze, M., and Limbird, L. E. (1997) *Proc Natl Acad Sci USA* 94, 9950–9955).

The above studies indicate that a polymorphism resulting in a markedly depressed alpha-2AAR function in humans would likely be of physiologic importance. Indeed, such a polymorphism can be a significant risk factor for hypertension. However, the one coding block polymorphism that we found in Caucasians and African-Americans is not associated with essential hypertension and in fact its phenotype is a gain of function. It should be noted that with our sample size we have the power to detect a polymorphism with an allele frequency of 0.04 with a statistical certainty of 90%, thus it is unlikely that we have failed to detect another polymorphism that is common in any of the cohorts. Based on the phenotype of the Lys251 receptor, and the known physiologic function of the alpha-2AAR, one can predict that the polymorphism would predispose to autonomic dysfunction characterized by hypotension and bradycardia. Similarly, patients with essential hypertension who have the polymorphism can have milder disease or display enhanced efficacy of antihypertensive agents such as clonidine or guanabenz. Interestingly, these individuals may display more pronounced central nervous system side-effects from these agents, such as sedation, which could ultimately limit their therapeutic utility. Finally, the hyperfunctioning polymorphism would be predicted to result in less norepinephrine release from cardiac sympathetic nerves, thereby potentially providing protection against the deleterious effects of catecholamines in patients with heart failure.

Mutations of G-protein coupled receptors are the basis of a number of rare diseases (Spiegel, A. M. (1996) *Annu Rev Physiol* 58, 143–170). In contrast, polymorphisms (allele frequencies >1%) of these receptors have been identified which can be minor risk factors for complex diseases (Kotanko, P., Binder, A., Tasker, J., DeFreitas, P., Kamdar, S., Clark, A. J., Skrabal, F., and Caulfield, M. (1997) *Hypertension* 30, 773–776), but more importantly act as disease modifiers ( Liggett, S. B., Wagoner, L. E., Craft, L. L., Hornung, R. W., Hoit, B. D., McIntosh, T. C., and Walsh, R. A. (1998) *J Clin Invest* 102, 1534–1539) or alter response to therapeutic agents targeting the receptor (Tan, S., Hall, I. P., Dewar, J., Dow, E., and Lipworth, B. (1997) *Lancet* 350, 995–999). Interestingly, when such mutations or polymorphisms have been found to alter function, the minor allelic variant (i.e., the least common form of the receptor) results in either decreased agonist-promoted function or increased non-agonist dependent function (i.e., constitutive activation). An example of the former is the Ile164 polymorphisms of the $\beta_2$A, which imparts defective agonist-promoted coupling to $G_s$ (Green, S. A., Cole, G., Jacinto, M., Innis, M., and Liggett, S. B. (1993) *J Biol Chem* 268, 23116–23121). Constitutive activation results in receptors adopting a mutation induced agonist-bound like state and thus signaling becomes independent of agonist. Such persistent activation is the pathologic basis for diseases such as male precocious puberty, which is due to a mutation in the leutinizing hormone receptor (Shenker, A., Laue, L., Kosugi, S., Merendino, J. J., Minegishi, T., and Cutler, G. B. (1993) *Nature Lond* 365, 652–654). In the current report we show that the Lys251 receptor does not exhibit constitutive activation, based on wild-type [$^3$S]GTP$\gamma$S binding, adenylyl cyclase, and MAP kinase activities in the absence of agonist. Instead, the phenotype that we observed was one of increased agonist-promoted function. To our knowledge this is the first delineation of a polymorphism of a pharmacogenetic locus of any G-protein coupled receptor where the minor allele displays this property, and thus this represents a new class of polymorphism for the superfamily.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for identifying a human at increased risk for developing a physiological function associated with an alpha-2A adrenergic receptor molecule comprising a lysine at amino acid 251, said method comprising the steps of obtaining information associated with a sample from the human, said information indicating the presence or absence of lysine at amino acid 251 of an alpha-2A adrenergic receptor molecule; and identifying the human at increased risk for the physiological function if lysine is present at amino acid 251 of alpha-2A adrenergic receptor molecule, wherein the physiological function is selected from an enhanced inhibition of adenylyl cyclase and enhanced stimulation of MAP kinase by the alpha-2A adrenergic receptor in response to an agonist, wherein the agonist is selected from the group consisting of a catecholamine, an azepine, and an imadazoline.

2. The method of claim 1, wherein said information is obtained using a nucleic acid based assay.

3. The method of claim 1, wherein the agonist is a catecholamine.

4. The method of claim 1, wherein the agonist is an azepine.

5. The method of claim 1, wherein the agonist is an imadazoline.

* * * * *